United States Patent
Wands et al.

(12)

(10) Patent No.: US 6,812,206 B2
(45) Date of Patent: Nov. 2, 2004

(54) DIAGNOSIS AND TREATMENT OF MALIGNANT NEOPLASMS

(75) Inventors: Jack R. Wands, Waban, MA (US); Suzanne M. de la Monte, East Greenwich, RI (US); Nedim Ince, Boston, MA (US); Rolf I. Carlson, Boston, MA (US)

(73) Assignee: Rhode Island Hospital, Providence, RI (US)

( * ) Notice: Subject to any disclaimer, the term of this patent is extended or adjusted under 35 U.S.C. 154(b) by 0 days.

(21) Appl. No.: 09/903,216

(22) Filed: Jul. 11, 2001

(65) Prior Publication Data

US 2002/0114811 A1 Aug. 22, 2002

Related U.S. Application Data

(62) Division of application No. 09/436,184, filed on Nov. 8, 1999.

(51) Int. Cl.$^7$ ........................ A61K 39/395; A61K 38/16
(52) U.S. Cl. ........................................ 514/2; 424/141.1
(58) Field of Search ......................... 424/141.1, 130.1, 424/134.1, 135.1, 138.1, 139.1, 152.1; 514/2, 44; 530/387.1

(56) References Cited

U.S. PATENT DOCUMENTS

| | | | |
|---|---|---|---|
| 5,789,426 A | * | 8/1998 | Hanauske-Abel et al. |
| 5,814,500 A | * | 9/1998 | Dietz |
| 5,851,999 A | * | 12/1998 | Ullrich et al. |
| 6,166,176 A | | 12/2000 | Radosevich |

FOREIGN PATENT DOCUMENTS

EP 180188 * 4/1992

OTHER PUBLICATIONS

Clark (Protein Engineering of Antibody Molecules for Prophylactic and Therapeutic Applications in Man, 1993, p. 1).*
DeWys et al (Cancer chemotherapy Reports, 1973, Part 1, vol. 57, pp. 41–49.*
Sinkule et al (Tumour Biology, 1991, vol. 12, pp. 198–206).*
Schlom (Monoclonal Antibodies: They're More and Less Than You Think, In: Molecular Foundations of Oncology, 1991, Ed. S. Broder, pp. 95–134).*
Kerr and Thorpe, Immunochemistry LabFax, 1994, p. 193.*
Aster, J. et al. (1994). *Cold Spring Harb. Symp. Uant. Biol.* 59: 125–136.
Ausubel, F. et al. (1990). Current Protocols in Molecular Biology vol. 2, John Wiley & Sons.
Capobianco, A. et al. (1997). *Mol. and Cell. Bio. 17*: 6265–6273.
Czubayko, F. et al. (1994). *J. Biol. Chem. 269*: 21358–21363.

de la Monte, S. et al. (1999). *Alcohol Clin. Exp. Res. 23*: 770–777.
Ghose, T. et al. (1983). *Methods in Enzymology 93*: 326–327.
Gronke, R. et al. (1990). *J. Biol. Chem. 265*: 8558–8565.
Gronke, R. et al. (1989). *Proc. Natl. Acad. Sci. USA 86*: 3609–3613.
Gual, P. et al. (1996). *Endocrinology 137*: 3416–3423.
Hansen, T. et al. (1989). *Proc. Natl. Acad. Sci. USA 86*: 3123–3126.
Higgins, D. and Sharp, P. (1989). *CABIOS 5*: 151–153.
Jia, S. et al. (1992). *J. Biol. Chem. 267*: 14322–14327.
Jia, S. et al. (1994). *Proc. Natl. Acad. Sci. USA 91*: 7227–7231.
Kelley, M. et al. (1987). *Cell 51*: 539–548.
Kobayashi, H. et al. (1994). *Cancer Research 54*: 1271–1275.
Korioth, F. et al. (1994). *Gene 150*: 395–399.
Lam, K. et al. (1994). *J. Biol. Chem. 269*: 20648–20652.
Lardelli, M. et al. (1994). *Mechanisms of Development 46*: 123–126.
Lavaisierre, L. et al. (1996). *J. Clin. Invest. 98*: 1313–1323.
Lecka–Czernik, B. et al. (1995). *Mol. and Cell. Bio. 15*: 120–128.
Levy–Toledano, R. et al. (1994). *EMBO J. 13*: 835–842.
Li, J. et al. (1999). *J. Biol. Chem. 274*: 9351–9356.
Mahieu, M. et al. (1994). *Blood 84*: 3758–3765.
Marasco, W. et al. (1993). *Proc. Natl. Acad. Sci. USA 90*: 7889–7893.
Marasco, W. (1997). *Gene Therapy 4*: 11–15.
McGinnis, K. et al. (1996). *Biochemistry 35*: 3957–3962.
McGinnis, K. et al. (1998). *Biochimica et Biophysica Acta 1387*:454–456.
Rozen, F. and Pollak, M. (1999). *Int. J. Oncol. 15*: 589–594.
Song, W. et al. (1999). *Proc. Natl. Acad. Sci. USA 96*: 6959–6963.
Sullivan, S. et al. (1994). *J. of Invest. Dermatol.103*: Supplement 85S–89S.
van de Poll, M. et al. (1998). *J. Biol. Chem. 273*: 16075–16081.
Wang, Q. et al. (1991). *J. Biol. Chem. 266*: 14004–14010.
Zhang, J. et al. (1999). *Analytical Biochemistry 271*: 137–142.
De La Monte, S. et al. (1999). *Modern Pathology 12*: 170A.
Ince, N. et al. (1997). *Hepatology 26(4)*: 362A.

(List continued on next page.)

*Primary Examiner*—Karen A. Canella
(74) *Attorney, Agent, or Firm*—Ingrid A. Beattie; Mintz, Levin, Cohn, Ferns, Glovsky and Popeo, P.C.

(57) ABSTRACT

The invention features a method for diagnosing a malignant neoplasm in a mammal by contacting a bodily fluid from the mammal with an antibody which binds to an human aspartyl (asparaginyl) beta-hydroxylase (HAAH) polypeptide and methods of treating malignant neoplasms by inhibiting HAAH.

14 Claims, 9 Drawing Sheets

OTHER PUBLICATIONS

Ince, N. et al. (2000). *Cancer Research 60*: 1261–1266.
Nishimaki, H. et al. (1999). *Jikeikai Medical Journal 46*: 129–136.
Nishimaki, H. et al. (1997). *Gastroenterology 112*(4)Supp.: A628.
International Search Report, issued Jun. 5, 2001.
Branch, A. (1996). *Hepatology 24*: 1517–1529.
Broaddus, W. et al. (2000). *Methods in Enzymology 314*: 121–135.
Jones, S. and Marasco, W. (1998). *Advanced Drug Delivery Reviews 31*: 153–170.
Hagemeijer, A. (1992). *Leukemia 6*: 16–18.

* cited by examiner

SEQUENCE LISTING

<160> NUMBER OF SEQ ID NOS: 9

<210> SEQ ID NO 1
<211> LENGTH: 36
<212> TYPE: PRT
<213> ORGANISM: Artificial Sequence
<220> FEATURE:
<223> OTHER INFORMATION: Description of Artificial Sequence: Consensus
      EGF-like domain
<221> NAME/KEY: VARIANT
<222> LOCATION: (2)..(8)
<223> OTHER INFORMATION: Wherein  Xaa is any amino acid
<221> NAME/KEY: VARIANT
<222> LOCATION: (10)..(13)
<223> OTHER INFORMATION: Wherein Xaa is any amino acid.
<221> NAME/KEY: VARIANT
<222> LOCATION: (15)..(24)
<223> OTHER INFORMATION: Wherein Xaa is any amino acid.
<221> NAME/KEY: VARIANT
<222> LOCATION: (26)
<223> OTHER INFORMATION: Wherein Xaa is any amino acid.
<221> NAME/KEY: VARIANT
<222> LOCATION: (28)..(35)
<223> OTHER INFORMATION: Wherein Xaa is any amino acid.

<400> SEQUENCE: 1

Cys Xaa Xaa Xaa Xaa Xaa Xaa Xaa Cys Xaa Xaa Xaa Xaa Cys Xaa Xaa
 1               5                  10                  15

Xaa Xaa Xaa Xaa Xaa Xaa Xaa Xaa Cys Xaa Cys Xaa Xaa Xaa Xaa Xaa
                20                  25                  30

Xaa Xaa Xaa Cys
         35

<210> SEQ ID NO 2
<211> LENGTH: 758
<212> TYPE: PRT
<213> ORGANISM: Homo sapiens

<400> SEQUENCE: 2

Met Ala Gln Arg Lys Asn Ala Lys Ser Ser Gly Asn Ser Ser Ser Ser
 1               5                  10                  15

Gly Ser Gly Ser Gly Ser Thr Ser Ala Gly Ser Ser Ser Pro Gly Ala
                20                  25                  30

Arg Arg Glu Thr Lys His Gly Gly His Lys Asn Gly Arg Lys Gly Gly
             35                  40                  45

Leu Ser Gly Thr Ser Phe Phe Thr Trp Phe Met Val Ile Ala Leu Leu
     50                  55                  60

Gly Val Trp Thr Ser Val Ala Val Val Trp Phe Asp Leu Val Asp Tyr
 65                  70                  75                  80

-continued

```
Glu Glu Val Leu Gly Lys Leu Gly Ile Tyr Asp Ala Asp Gly Asp Gly
                85                  90                  95

Asp Phe Asp Val Asp Asp Ala Lys Val Leu Leu Gly Leu Lys Glu Arg
               100                 105                 110

Ser Thr Ser Glu Pro Ala Val Pro Pro Glu Glu Ala Glu Pro His Thr
           115                 120                 125

Glu Pro Glu Glu Gln Val Pro Val Glu Ala Glu Pro Gln Asn Ile Glu
       130                 135                 140

Asp Glu Ala Lys Glu Gln Ile Gln Ser Leu Leu His Glu Met Val His
145                 150                 155                 160

Ala Glu His Val Glu Gly Glu Asp Leu Gln Gln Glu Asp Gly Pro Thr
               165                 170                 175

Gly Glu Pro Gln Gln Glu Asp Asp Glu Phe Leu Met Ala Thr Asp Val
           180                 185                 190

Asp Asp Arg Phe Glu Thr Leu Glu Pro Glu Val Ser His Glu Glu Thr
       195                 200                 205

Glu His Ser Tyr His Val Glu Glu Thr Val Ser Gln Asp Cys Asn Gln
   210                 215                 220

Asp Met Glu Glu Met Met Ser Glu Gln Glu Asn Pro Asp Ser Ser Glu
225                 230                 235                 240

Pro Val Val Glu Asp Glu Arg Leu His His Asp Thr Asp Asp Val Thr
               245                 250                 255

Tyr Gln Val Tyr Glu Glu Gln Ala Val Tyr Glu Pro Leu Glu Asn Glu
           260                 265                 270

Gly Ile Glu Ile Thr Glu Val Thr Ala Pro Pro Glu Asp Asn Pro Val
       275                 280                 285

Glu Asp Ser Gln Val Ile Val Glu Glu Val Ser Ile Phe Pro Val Glu
   290                 295                 300

Glu Gln Gln Glu Val Pro Pro Glu Thr Asn Arg Lys Thr Asp Asp Pro
305                 310                 315                 320

Glu Gln Lys Ala Lys Val Lys Lys Lys Pro Lys Leu Leu Asn Lys
               325                 330                 335

Phe Asp Lys Thr Ile Lys Ala Glu Leu Asp Ala Ala Glu Lys Leu Arg
           340                 345                 350

Lys Arg Gly Lys Ile Glu Glu Ala Val Asn Ala Phe Lys Glu Leu Val
       355                 360                 365

Arg Lys Tyr Pro Gln Ser Pro Arg Ala Arg Tyr Gly Lys Ala Gln Cys
   370                 375                 380

Glu Asp Asp Leu Ala Glu Lys Arg Arg Ser Asn Glu Val Leu Arg Gly
385                 390                 395                 400

Ala Ile Glu Thr Tyr Gln Glu Val Ala Ser Leu Pro Asp Val Pro Ala
               405                 410                 415

Asp Leu Leu Lys Leu Ser Leu Lys Arg Arg Ser Asp Arg Gln Gln Phe
           420                 425                 430

Leu Gly His Met Arg Gly Ser Leu Leu Thr Leu Gln Arg Leu Val Gln
       435                 440                 445

Leu Phe Pro Asn Asp Thr Ser Leu Lys Asn Asp Leu Gly Val Gly Tyr
   450                 455                 460

Leu Leu Ile Gly Asp Asn Asp Asn Ala Lys Lys Val Tyr Glu Glu Val
465                 470                 475                 480

Leu Ser Val Thr Pro Asn Asp Gly Phe Ala Lys Val His Tyr Gly Phe
               485                 490                 495

Ile Leu Lys Ala Gln Asn Lys Ile Ala Glu Ser Ile Pro Tyr Leu Lys
```

```
              500                 505                 510
Glu Gly Ile Glu Ser Gly Asp Pro Gly Thr Asp Asp Gly Arg Phe Tyr
        515                 520                 525

Phe His Leu Gly Asp Ala Met Gln Arg Val Gly Asn Lys Glu Ala Tyr
        530                 535                 540

Lys Trp Tyr Glu Leu Gly His Lys Arg Gly His Phe Ala Ser Val Trp
545                 550                 555                 560

Gln Arg Ser Leu Tyr Asn Val Asn Gly Leu Lys Ala Gln Pro Trp Trp
                565                 570                 575

Thr Pro Lys Glu Thr Gly Tyr Thr Glu Leu Val Lys Ser Leu Glu Arg
            580                 585                 590

Asn Trp Lys Leu Ile Arg Asp Glu Gly Leu Ala Val Met Asp Lys Ala
        595                 600                 605

Lys Gly Leu Phe Leu Pro Glu Asp Glu Asn Leu Arg Glu Lys Gly Asp
    610                 615                 620

Trp Ser Gln Phe Thr Leu Trp Gln Gln Gly Arg Arg Asn Glu Asn Ala
625                 630                 635                 640

Cys Lys Gly Ala Pro Lys Thr Cys Thr Leu Leu Glu Lys Phe Pro Glu
                645                 650                 655

Thr Thr Gly Cys Arg Arg Gly Gln Ile Lys Tyr Ser Ile Met His Pro
            660                 665                 670

Gly Thr His Val Trp Pro His Thr Gly Pro Thr Asn Cys Arg Leu Arg
        675                 680                 685

Met His Leu Gly Leu Val Ile Pro Lys Glu Gly Cys Lys Ile Arg Cys
    690                 695                 700

Ala Asn Glu Thr Arg Thr Trp Glu Glu Gly Lys Val Leu Ile Phe Asp
705                 710                 715                 720

Asp Ser Phe Glu His Glu Val Trp Gln Asp Ala Ser Ser Phe Arg Leu
                725                 730                 735

Ile Phe Ile Val Asp Val Trp His Pro Glu Leu Thr Pro Gln Gln Arg
            740                 745                 750

Arg Ser Leu Pro Ala Ile
        755

<210> SEQ ID NO 3
<211> LENGTH: 2324
<212> TYPE: DNA
<213> ORGANISM: Homo sapiens

<400> SEQUENCE: 3
cggaccgtgc aatggcccag cgtaagaatg ccaagagcag cggcaacagc agcagcagcg      60
gctccggcag cggtagcacg agtgcgggca gcagcagccc cggggcccgg agagagacaa     120
agcatggagg acacaagaat gggaggaaag gcggactctc gggaacttca ttcttcacgt     180
ggtttatggt gattgcattg ctgggcgtct ggacatctgt agctgtcgtt tggtttgatc     240
ttgttgacta tgaggaagtt ctaggaaaac taggaatcta tgatgctgat ggtgatggag     300
attttgatgt ggatgatgcc aaagttttat taggacttaa agagagatct acttcagagc     360
cagcagtccc gccagaagag gctgagccac acactgagcc cgaggagcag gttcctgtgg     420
aggcagaacc ccagaatatc gaagatgaag caaaagaaca aattcagtcc cttctccatg     480
aaatggtaca cgcagaacat gttgagggag aagacttgca acaagaagat ggacccacag     540
gagaaccaca acaagaggat gatgagtttc ttatggcgac tgatgtagat gatagatttg     600
agaccctgga acctgaagta tctcatgaag aaaccgagca tagttaccac gtggaagaga     660
```

-continued

```
cagtttcaca agactgtaat caggatatgg aagagatgat gtctgagcag gaaaatccag      720
attccagtga accagtagta aagatgaaa gattgcacca tgatacagat gatgtaacat      780
accaagtcta tgaggaacaa gcagtatatg aacctctaga aaatgaaggg atagaaatca      840
cagaagtaac tgctccccct gaggataatc ctgtagaaga ttcacaggta attgtagaag      900
aagtaagcat ttttcctgtg aagaacagc aggaagtacc accagaaaca aatagaaaaa      960
cagatgatcc agaacaaaaa gcaaaagtta agaaaaagaa gcctaaactt ttaaataaat     1020
ttgataagac tattaaagct gaacttgatg ctgcagaaaa actccgtaaa agggaaaaa     1080
ttgaggaagc agtgaatgca tttaaagaac tagtacgcaa atacctcag agtccacgag      1140
caagatatgg gaaggcgcag tgtgaggatg atttggctga agagaggaga agtaatgagg      1200
tgctacgtgg agccatcgag acctaccaag aggtggccag cctacctgat gtccctgcag      1260
acctgctgaa gctgagtttg aagcgtcgct cagacaggca acaatttcta ggtcatatga     1320
gaggttccct gcttaccctg cagagattag ttcaactatt tcccaatgat acttccttaa      1380
aaaatgacct tggcgtggga tacctcttga taggagataa tgacaatgca aagaaagttt     1440
atgaagaggt gctgagtgtg cacctaatg atggctttgc taaagtccat tatggcttca      1500
tcctgaaggc acagaacaaa attgctgaga gcatcccata tttaaaggaa ggaatagaat      1560
ccggagatcc tggcactgat gatgggagat tttatttcca cctgggggat gccatgcaga      1620
gggttgggaa caaagaggca tataagtggt atgagcttgg gcacaagaga ggacactttg      1680
catctgtctg gcaacgctca ctctacaatg tgaatggact gaaagcacag ccttggtgga      1740
ccccaaaaga aacgggctac acagagttag taaagtcttt agaaagaaac tggaagttaa      1800
tccgagatga aggccttgca gtgatggata agccaaagg tctcttcctg cctgaggatg      1860
aaaacctgag ggaaaaaggg gactggagcc agttcacgct gtggcagcaa ggaagaagaa      1920
atgaaaatgc ctgcaaagga gctcctaaaa cctgtacctt actagaaaag ttccccgaga      1980
caacaggatg cagaagagga cagatcaaat attccatcat gcaccccggg actcacgtgt      2040
ggccgcacac agggcccaca aactgcaggc tccgaatgca cctgggcttg gtgattccca      2100
aggaaggctg caagattcga tgtgccaacg agaccaggac ctgggaggaa ggcaaggtgc      2160
tcatctttga tgactccttt gagcacgagg tatggcagga tgcctcatct ttccggctga      2220
tattcatcgt ggatgtgtgg catccggaac tgacaccaca gcagagacgc agccttccag      2280
caatttagca tgaattcatg caagcttggg aaactctgga gaga               2324
```

```
<210> SEQ ID NO 4
<211> LENGTH: 31
<212> TYPE: PRT
<213> ORGANISM: Artificial Sequence
<220> FEATURE:
<223> OTHER INFORMATION: Description of Artificial Sequence: EGF-like
      cysteine-rich repeat
<221> NAME/KEY: VARIANT
<222> LOCATION: (3)..(5)
<223> OTHER INFORMATION: Wherein any Xaa may be any amino acid
<221> NAME/KEY: VARIANT
<222> LOCATION: (6)..(7)
<223> OTHER INFORMATION: Wherein Xaa is any amino acid.
<221> NAME/KEY: VARIANT
<222> LOCATION: (10)
<223> OTHER INFORMATION: Wherein Xaa is any amino acid.
<221> NAME/KEY: VARIANT
<222> LOCATION: (14)
<223> OTHER INFORMATION: Wherein Xaa is any amino acid.
<221> NAME/KEY: VARIANT
<222> LOCATION: (17)..(18)
```

```
<221> NAME/KEY: VARIANT
<222> LOCATION: (25)..(26)
<223> OTHER INFORMATION: Wherein Xaa is any amino acid.
<221> NAME/KEY: VARIANT
<222> LOCATION: (29)
<223> OTHER INFORMATION: Wherein Xaa is any amino acid.

<400> SEQUENCE: 4

Cys Asp Xaa Xaa Xaa Cys Xaa Xaa Lys Xaa Gly Asn Gly Xaa Cys Asp
 1               5                  10                  15

Xaa Xaa Cys Asn Asn Ala Ala Cys Xaa Xaa Asp Gly Xaa Asp Cys
            20                  25                  30

<210> SEQ ID NO 5
<211> LENGTH: 1242
<212> TYPE: PRT
<213> ORGANISM: Homo sapiens

<400> SEQUENCE: 5

Met Ala Ser Pro Pro Glu Ser Asp Gly Phe Ser Asp Val Arg Lys Val
 1               5                  10                  15

Gly Tyr Leu Arg Lys Pro Lys Ser Met His Lys Arg Phe Phe Val Leu
            20                  25                  30

Arg Ala Ala Ser Glu Ala Gly Gly Pro Ala Arg Leu Glu Tyr Tyr Glu
        35                  40                  45

Asn Glu Lys Lys Trp Arg His Lys Ser Ser Ala Pro Lys Arg Ser Ile
    50                  55                  60

Pro Leu Glu Ser Cys Phe Asn Ile Asn Lys Arg Ala Asp Ser Lys Asn
65                  70                  75                  80

Lys His Leu Val Ala Leu Tyr Thr Arg Asp Glu His Phe Ala Ile Ala
                85                  90                  95

Ala Asp Ser Glu Ala Glu Gln Asp Ser Trp Tyr Gln Ala Leu Leu Gln
            100                 105                 110

Leu His Asn Arg Ala Lys Gly His His Asp Gly Ala Ala Ala Leu Gly
        115                 120                 125

Ala Gly Gly Gly Gly Ser Cys Ser Gly Ser Ser Gly Leu Gly Glu
    130                 135                 140

Ala Gly Glu Asp Leu Ser Tyr Gly Asp Val Pro Pro Gly Pro Ala Phe
145                 150                 155                 160

Lys Glu Val Trp Gln Val Ile Leu Lys Pro Lys Gly Leu Gly Gln Thr
                165                 170                 175

Lys Asn Leu Ile Gly Ile Tyr Arg Leu Cys Leu Thr Ser Lys Thr Ile
            180                 185                 190

Ser Phe Val Lys Leu Asn Ser Glu Ala Ala Ala Val Val Leu Gln Leu
        195                 200                 205

Met Asn Ile Arg Arg Cys Gly His Ser Glu Asn Phe Phe Phe Ile Glu
    210                 215                 220

Val Gly Arg Ser Ala Val Thr Gly Pro Gly Glu Phe Trp Met Gln Val
225                 230                 235                 240

Asp Asp Ser Val Val Ala Gln Asn Met His Glu Thr Ile Leu Glu Ala
                245                 250                 255

Met Arg Ala Met Ser Asp Glu Phe Arg Pro Arg Ser Lys Ser Gln Ser
            260                 265                 270

Ser Ser Asn Cys Ser Asn Pro Ile Ser Val Pro Leu Arg Arg His His
        275                 280                 285

Leu Asn Asn Pro Pro Ser Gln Val Gly Leu Thr Arg Arg Ser Arg
    290                 295                 300
```

```
Thr Glu Ser Ile Thr Ala Thr Ser Pro Ala Ser Met Val Gly Gly Lys
305                 310                 315                 320

Pro Gly Ser Phe Arg Val Arg Ala Ser Ser Asp Gly Glu Gly Thr Met
            325                 330                 335

Ser Arg Pro Ala Ser Val Asp Gly Ser Pro Val Ser Pro Ser Thr Asn
            340                 345                 350

Arg Thr His Ala His Arg His Arg Gly Ser Ala Arg Leu His Pro Pro
        355                 360                 365

Leu Asn His Ser Arg Ser Ile Pro Met Pro Ala Ser Arg Cys Ser Pro
370                 375                 380

Ser Ala Thr Ser Pro Val Ser Leu Ser Ser Ser Thr Ser Gly His
385                 390                 395                 400

Gly Ser Thr Ser Asp Cys Leu Phe Pro Arg Arg Ser Ser Ala Ser Val
                405                 410                 415

Ser Gly Ser Pro Ser Asp Gly Gly Phe Ile Ser Ser Asp Glu Tyr Gly
            420                 425                 430

Ser Ser Pro Cys Asp Phe Arg Ser Ser Phe Arg Ser Val Thr Pro Asp
        435                 440                 445

Ser Leu Gly His Thr Pro Pro Ala Arg Gly Glu Glu Glu Leu Ser Asn
450                 455                 460

Tyr Ile Cys Met Gly Gly Lys Gly Pro Ser Thr Leu Thr Ala Pro Asn
465                 470                 475                 480

Gly His Tyr Ile Leu Ser Arg Gly Gly Asn Gly His Arg Cys Thr Pro
                485                 490                 495

Gly Thr Gly Leu Gly Thr Ser Pro Ala Leu Ala Gly Asp Glu Ala Ala
            500                 505                 510

Ser Ala Ala Asp Leu Asp Asn Arg Phe Arg Lys Arg Thr His Ser Ala
        515                 520                 525

Gly Thr Ser Pro Thr Ile Thr His Gln Lys Thr Pro Ser Gln Ser Ser
530                 535                 540

Val Ala Ser Ile Glu Glu Tyr Thr Glu Met Met Pro Ala Tyr Pro Pro
545                 550                 555                 560

Gly Gly Gly Ser Gly Gly Arg Leu Pro Gly His Arg His Ser Ala Phe
                565                 570                 575

Val Pro Thr Arg Ser Tyr Pro Glu Glu Gly Leu Glu Met His Pro Leu
            580                 585                 590

Glu Arg Arg Gly Gly His His Arg Pro Asp Ser Ser Thr Leu His Thr
        595                 600                 605

Asp Asp Gly Tyr Met Pro Met Ser Pro Gly Val Ala Pro Val Pro Ser
610                 615                 620

Gly Arg Lys Gly Ser Gly Asp Tyr Met Pro Met Ser Pro Lys Ser Val
625                 630                 635                 640

Ser Ala Pro Gln Gln Ile Ile Asn Pro Ile Arg Arg His Pro Gln Arg
                645                 650                 655

Val Asp Pro Asn Gly Tyr Met Met Met Ser Pro Ser Gly Gly Cys Ser
            660                 665                 670

Pro Asp Ile Gly Gly Gly Pro Ser Ser Ser Ser Ser Ser Asn Ala
        675                 680                 685

Val Pro Ser Gly Thr Ser Tyr Gly Lys Leu Trp Thr Asn Gly Val Gly
690                 695                 700

Gly His His Ser His Val Leu Pro His Pro Lys Pro Pro Val Glu Ser
705                 710                 715                 720
```

-continued

```
Ser Gly Gly Lys Leu Leu Pro Cys Thr Gly Asp Tyr Met Asn Met Ser
            725                 730                 735
Pro Val Gly Asp Ser Asn Thr Ser Ser Pro Ser Asp Cys Tyr Tyr Gly
            740                 745                 750
Pro Glu Asp Pro Gln His Lys Pro Val Leu Ser Tyr Tyr Ser Leu Pro
            755                 760                 765
Arg Ser Phe Lys His Thr Gln Arg Pro Gly Glu Pro Glu Gly Ala
            770                 775                 780
Arg His Gln His Leu Arg Leu Ser Thr Ser Ser Gly Arg Leu Leu Tyr
785                 790                 795                 800
Ala Ala Thr Ala Asp Ser Ser Ser Thr Ser Ser Asp Ser Leu
            805                 810                 815
Gly Gly Gly Tyr Cys Gly Ala Arg Leu Glu Pro Ser Leu Pro His Pro
            820                 825                 830
His His Gln Val Leu Gln Pro His Leu Pro Arg Lys Val Asp Thr Ala
            835                 840                 845
Ala Gln Thr Asn Ser Arg Leu Ala Arg Pro Thr Arg Leu Ser Leu Gly
            850                 855                 860
Asp Pro Lys Ala Ser Thr Leu Pro Arg Ala Arg Glu Gln Gln Gln Gln
865                 870                 875                 880
Gln Gln Pro Leu Leu His Pro Pro Glu Pro Lys Ser Pro Gly Glu Tyr
            885                 890                 895
Val Asn Ile Glu Phe Gly Ser Asp Gln Ser Gly Tyr Leu Ser Gly Pro
            900                 905                 910
Val Ala Phe His Ser Ser Pro Ser Val Arg Cys Pro Ser Gln Leu Gln
            915                 920                 925
Pro Ala Pro Arg Glu Glu Thr Gly Thr Glu Tyr Met Lys Met
            930                 935                 940
Asp Leu Gly Pro Gly Arg Arg Ala Ala Trp Gln Glu Ser Thr Gly Val
945                 950                 955                 960
Glu Met Gly Arg Leu Gly Pro Ala Pro Pro Gly Ala Ala Ser Ile Cys
            965                 970                 975
Arg Pro Thr Arg Ala Val Pro Ser Ser Arg Gly Asp Tyr Met Thr Met
            980                 985                 990
Gln Met Ser Cys Pro Arg Gln Ser Tyr Val Asp Thr Ser Pro Ala Ala
            995                 1000                1005
Pro Val Ser Tyr Ala Asp Met Arg Thr Gly Ile Ala Ala Glu Glu Val
            1010                1015                1020
Ser Leu Pro Arg Ala Thr Met Ala Ala Ala Ser Ser Ser Ala Ala
1025                1030                1035                1040
Ser Ala Ser Pro Thr Gly Pro Gln Gly Ala Ala Glu Leu Ala Ala His
            1045                1050                1055
Ser Ser Leu Leu Gly Gly Pro Gln Gly Pro Gly Gly Met Ser Ala Phe
            1060                1065                1070
Thr Arg Val Asn Leu Ser Pro Asn Arg Asn Gln Ser Ala Lys Val Ile
            1075                1080                1085
Arg Ala Asp Pro Gln Gly Cys Arg Arg His Ser Ser Glu Thr Phe
            1090                1095                1100
Ser Ser Thr Pro Ser Ala Thr Arg Val Gly Asn Thr Val Pro Phe Gly
1105                1110                1115                1120
Ala Gly Ala Ala Val Gly Gly Gly Gly Ser Ser Ser Ser Glu
            1125                1130                1135
Asp Val Lys Arg His Ser Ser Ala Ser Phe Glu Asn Val Trp Leu Arg
```

```
            1140                1145                1150
Pro Gly Glu Leu Gly Gly Ala Pro Lys Glu Pro Ala Lys Leu Cys Gly
        1155                1160                1165

Ala Ala Gly Gly Leu Glu Asn Gly Leu Asn Tyr Ile Asp Leu Asp Leu
    1170                1175                1180

Val Lys Asp Phe Lys Gln Cys Pro Gln Glu Cys Thr Pro Glu Pro Gln
1185                1190                1195                1200

Pro Pro Pro Pro Pro Pro His Gln Pro Leu Gly Ser Gly Glu Ser
            1205                1210                1215

Ser Ser Thr Arg Arg Ser Ser Glu Asp Leu Ser Ala Tyr Ala Ser Ile
        1220                1225                1230

Ser Phe Gln Lys Gln Pro Glu Asp Arg Gln
        1235                1240

<210> SEQ ID NO 6
<211> LENGTH: 5828
<212> TYPE: DNA
<213> ORGANISM: Homo sapiens

<400> SEQUENCE: 6
cggcggcgcg gtcggagggg gccggcgcgc agagccagac gccgccgctt gttttggttg     60
gggctctcgg caactctccg aggaggagga ggaggaggga ggaggggaga agtaactgca    120
gcggcagcgc cctcccgagg aacaggcgtc ttccccgaac ccttcccaaa cctcccccat    180
cccctctcgc ccttgtcccc tcccctcctc cccagccgcc tggagcgagg ggcagggatg    240
agtctgtccc tccggccggt ccccagctgc agtggctgcc cggtatcgtt tcgcatggaa    300
aagccacttt ctccacccgc cgagatgggc ccggatgggg ctgcagagga cgcgcccgcg    360
gcggcggca gcagcagcag cagcagcagc agcaacagca acagccgcag cgccgcggtc    420
tctgcgactg agctggtatt tgggcggctg gtggcggctg ggacggttgg ggggtgggag    480
gaggcgaagg aggagggaga accccgtgca acgttgggac ttggcaaccc gcctcccct     540
gcccaaggat atttaatttg cctcgggaat cgctgcttcc agaggggaac tcaggaggga    600
aggcgcgcgc gcgcgcgcgc tcctggaggg gcaccgcagg gaccccgac tgtcgcctcc     660
ctgtgccgga ctccagccgg ggcgacgaga atgcatctt cgctccttcc tggtggcggc    720
ggcggctgag aggagacttg gctctcggag gatcggggct gccctcaccc cggacgcact    780
gcctccccgc cggcgtgaag cgcccgaaaa ctccggtcgg gctctctcct gggctcagca    840
gctgcgtcct ccttcagctg cccctccccg gcgcgggggg cggcgtggat ttcagagtcg    900
gggtttctgc tgcctccagc cctgtttgca tgtgccgggc gcggcgagg agcctccgcc     960
ccccacccgg ttgttttttcg gagcctcccct ctgctcagcg ttggtggtgg cggtggcagc   1020
atggcgagcc ctccggagag cgatggcttc tcggacgtgc gcaaggtggg ctacctgcgc    1080
aaacccaaga gcatgcacaa acgcttcttc gtactgcgcg cggccagcga ggctgggggc    1140
ccggcgcgcc tcgagtacta cgagaacgag aagaagtggc ggcacaagtc gagcgccccc    1200
aaacgctcga tccccttga gagctgcttc aacatcaaca gcgggctga ctccaagaac     1260
aagcacctgg tggctctcta cacccgggac gagcactttg ccatcgcggc ggacagcgag    1320
gccgagcaag acagctggta ccaggctctc tacagctgc acaacgtgc taagggccac    1380
cacgacggag ctgcggccct cggggcggga ggtggtgggg gcagctgcag cggcagctcc    1440
ggccttggtg aggctgggga ggacttgagc tacggtgacg tgcccccagg acccgcattc    1500
aaagaggtct ggcaagtgat cctgaagccc aagggcctgg gtcagacaaa gaacctgatt    1560
```

-continued

```
ggtatctacc gcctttgcct gaccagcaag accatcagct tcgtgaagct gaactcggag    1620
gcagcggccg tggtgctgca gctgatgaac atcaggcgct gtggccactc ggaaaacttc    1680
ttcttcatcg aggtgggccg ttctgccgtg acggggcccg gggagttctg gatgcaggtg    1740
gatgactctg tggtggccca gaacatgcac gagaccatcc tggaggccat gcgggccatg    1800
agtgatgagt ccgccctcg cagcaagagc cagtcctcgt ccaactgctc taaccccatc     1860
agcgtccccc tgcgccggca ccatctcaac aatcccccgc ccagccaggt ggggctgacc    1920
cgccgatcac gcactgagag catcaccgcc acctccccgg ccagcatggt gggcgggaag    1980
ccaggctcct tccgtgtccg cgcctccagt gacggcgaag gcaccatgtc ccgcccagcc    2040
tcggtggacg gcagccctgt gagtcccagc accaacagaa cccacgccca ccggcatcgg    2100
ggcagcgccc ggctgcaccc cccgctcaac acagccgct ccatccccat gccggcttcc     2160
cgctgctcgc cttcggccac cagcccggtc agtctgtcgt ccagtagcac cagtggccat    2220
ggctccacct cggattgtct cttcccacgg cgatctagtg cttcggtgtc tggttccccc    2280
agcgatggcg gtttcatctc ctcggatgag tatggctcca gtccctgcga tttccggagt    2340
tccttccgca gtgtcactcc ggattccctg gccacaccc accagcccg cggtgaggag      2400 gagctaagca actatatctg catgggtggc aaggggccct ccaccctgac cgcccccaac    2460
ggtcactaca ttttgtctcg gggtggcaat ggccaccgct gcaccccagg aacaggcttg    2520
ggcacgagtc cagccttggc tgggatgaa gcagccagtg ctgcagatct ggataatcgg     2580
ttccgaaaga gaactcactc ggcaggcaca tcccctacca ttacccacca gaagaccccg    2640
tcccagtcct cagtggcttc cattgaggag tacacagaga tgatgcctgc ctacccacca    2700
ggaggtggca gtgaggccg actgccggga cacaggcact ccgccttcgt gcccacccgc     2760
tcctacccag aggagggtct ggaaatgcac cccttggagc gtcgggggg gcaccaccgc     2820 ccagacagct ccaccctcca cacgatgat ggctacatgc ccatgtcccc aggggtggcc     2880
ccagtgccca gtggccgaaa gggcagtgga gactatatgc ccatgagccc caagagcgta    2940
tctgccccac agcagatcat caatcccatc agacgccatc cccagagagt ggaccccaat    3000
ggctacatga tgatgtcccc cagcggtggc tgctctcctg acattggagg tggccccagc    3060
agcagcagca gcagcagcaa cgccgtccct tccgggacca gctatggaaa gctgtggaca    3120
aacggggtag ggggccacca ctctcatgtc ttgcctcacc ccaaaccccc agtggagagc    3180
agcggtggta agctcttacc ttgcacaggt gactacatga acatgtcacc agtgggggac    3240
tccaacacca gcagccctc cgactgctac tacggccctg aggacccca gcacaagcca     3300 gtcctctcct actactcatt gccaagatcc tttaagcaca cccagcgccc cggggagccg    3360
gaggagggtg cccggcatca gcacctccgc ctttccacta gctctggtcg ccttctctat    3420
gctgcaacag cagatgattc ttcctcttcc accagcagcg acagcctggg tggggatac    3480 tgcgggcta ggctggagcc cagccttcca catccccacc atcaggttct gcagcccat      3540 ctgcctcgaa aggtggacac agctgctcag accaatagcc gcctggcccg gcccacgagg   3600
ctgtccctgg gggatcccaa ggccagcacc ttacctcggg cccgagagca gcagcagcag    3660
cagcagccct gctgcacccc tccagagccc aagagcccgg gggaatatgt caatattgaa    3720
tttgggagtg atcagtctgg ctacttgtct ggcccggtgg cttccacag ctcaccttct     3780 gtcaggtgtc catcccagct ccagccagct cccagagagg aagagactgg cactgaggag    3840
tacatgaaga tggacctggg gccgggccgg agggcagcct ggcaggagag cactgggtc     3900
```

-continued

```
gagatgggca gactgggccc tgcacctccc ggggctgcta gcatttgcag gcctacccgg      3960
gcagtgccca gcagccgggg tgactacatg accatgcaga tgagttgtcc ccgtcagagc      4020
tacgtggaca cctcgccagc tgcccctgta agctatgctg acatgcgaac aggcattgct      4080
gcagaggagg tgagcctgcc cagggccacc atggctgctg cctcctcatc ctcagcagcc      4140
tctgcttccc cgactgggcc tcaagggggca gcagagctgg ctgcccactc gtccctgctg      4200
gggggcccac aaggacctgg gggcatgagc gccttcaccc gggtgaacct cagtcctaac      4260
cgcaaccaga gtgccaaagt gatccgtgca gacccacaag ggtgccggcg gaggcatagc      4320
tccgagactt tctcctcaac acccagtgcc acccgggtgg gcaacacagt gcccttgga      4380 gcggggcag cagtagggg cggtggcggt agcagcagca gcagcgagga tgtgaaacgc      4440
cacagctctg cttcctttga gaatgtgtgg ctgaggcctg gggagcttgg gggagccccc      4500
aaggagccag ccaaactgtg tggggctgct gggggtttgg agaatggtct taactacata      4560
gacctggatt tggtcaagga cttcaaacag tgccctcagg agtgcacccc tgaaccgcag      4620
cctcccccac ccccacccccc tcatcaaccc ctgggcagcg gtgagagcag ctccacccgc      4680
cgctcaagtg aggatttaag cgcctatgcc agcatcagtt ccagaagca gccagaggac      4740 cgtcagtagc tcaactggac atcacagcag aatgaagacc taaatgacct cagcaaatcc      4800
tcttctaact catgggtacc cagactctaa atatttcatg attcacaact aggacctcat      4860
atcttcctca tcagtagatg gtacgatgca tccatttcag tttgtttact ttatccaatc      4920
ctcaggattt cattgactga actgcacgtt ctatattgtg ccaagcgaaa aaaaaaaatg      4980
cactgtgaca ccagaataat gagtctgcat aaacttcatc ttcaaccta aggacttagc      5040 tggccacagt gagctgatgt gcccaccacc gtgtcatgag agaatgggtt tactctcaat      5100
gcattttcaa gatacatttc atctgctgct gaaactgtgt acgacaaagc atcattgtaa      5160
attatttcat acaaaactgt tcacgttggg tggagagagt attaaatatt taacataggt      5220
tttgatttat atgtgtaatt ttttaaatga aatgtaact tttcttacag cacatctttt      5280
ttttggatgt gggatggagg tatacaatgt tctgttgtaa agagtggagc aaatgcttaa      5340
aacaaggctt aaaagagtag aatagggtat gatccttgtt ttaagattgt aattcagaaa      5400
acataatata agaatcatag tgccatagat ggttctcaat tgtatagtta tatttgctga      5460
tactatctct tgtcatataa acctgatgtt gagctgagtt ccttataaga attaatctta      5520
attttgtatt ttttcctgta agacaatagg ccatgttaat taaactgaag aaggatatat      5580
ttggctgggt gttttcaaat gtcagcttaa aattggtaat tgaatggaag caaaattata      5640
agaagaggaa attaaagtct tccattgcat gtattgtaaa cagaaggaga tgggtgattc      5700
cttcaattca aaagctctct ttggaatgaa caatgtgggc gtttgtaaat tctggaaatg      5760
tctttctatt cataataaac tagatactgt tgatcttta aaaaaaaaa aaaaaaaaa      5820 aaaaaaaa                                                              5828
```

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: FLAG
      epitope

<400> SEQUENCE: 7

Asp Tyr Lys Asp Asp Asp Asp Lys
 1               5

```
<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence:Primer

<400> SEQUENCE: 8
gggggaattt gtcaata                                              17

<210> SEQ ID NO 9
<211> LENGTH: 16
<212> TYPE: DNA
<213> ORGANISM: Artificial Sequence
<220> FEATURE:
<223> OTHER INFORMATION: Description of Artificial Sequence:Primer

<400> SEQUENCE: 9
gaatttgtta atattg                                               16
```

DIAGNOSIS AND TREATMENT OF MALIGNANT NEOPLASMS

This application is a divisional of patent application U.S. Ser. No. 09/436,184, filed on Nov. 8, 1999, the entire contents of which is hereby incorporated by reference.

STATEMENT AS TO FEDERALLY SPONSORED RESEARCH

This invention was made with U.S. Government support under National Institutes of Health grants CA-35711, AA-02666, AA-02169, and AA11431. The government has certain rights in the invention.

BACKGROUND OF THE INVENTION

Primary malignant central nervous system (CNS) neoplasms, particularly glioblastomas, are highly fatal due to their aggressive and widespread infiltration of the brain and resistance to anti-cancer treatments. Although progress has been made in unraveling the pathological mechanisms underlying CNS cancers as well as other cancer types, tumor specific therapeutic approaches and methods of diagnosis have been largely elusive.

SUMMARY OF THE INVENTION

The invention features a method for diagnosing a malignant neoplasm in a mammal by contacting a bodily fluid from the mammal with an antibody which binds to an human aspartyl (asparaginyl) beta-hydroxylase (HAAH) polypeptide under conditions sufficient to form an antigen-antibody complex and detecting the antigen-antibody complex (for the purposes of this specification, HAAH polypeptide refers to the amino acid sequence of SEQ ID NO:2 and HAAH cDNA refers to the nucleotide sequence of SEQ ID NO:3). Malignant neoplasms detected in this manner include those derived from endodermal tissue, e.g., colon cancer, breast cancer, pancreatic cancer, liver cancer, and cancer of the bile ducts. Neoplasms of the central nervous system (CNS) such as primary malignant CNS neoplasms of both neuronal and glial cell origin and metastatic CNS neoplasms are also detected. Patient derived tissue samples, e.g., biopsies of solid tumors, as well as bodily fluids such as a CNS-derived bodily fluid, blood, serum, urine, saliva, sputum, lung effusion, and ascites fluid, are contacted with an HAAH-specific antibody.

The assay format is also useful to generate temporal data used for prognosis of malignant disease. A method for prognosis of a malignant neoplasm of a mammal is carried out by (a) contacting a bodily fluid from the mammal with an antibody which binds to an HAAH polypeptide under conditions sufficient to form an antigen-antibody complex and detecting the antigen-antibody complex; (b) quantitating the amount of complex to determine the level of HAAH in the fluid; and (c) comparing the level of HAAH in the fluid with a normal control level of HAAH. An increasing level of HAAH over time indicates a progressive worsening of the disease, and therefore, an adverse prognosis.

The invention also includes an antibody which binds to HAAH. The antibody preferably binds to a site in the carboxyterminal catalytic domain of HAAH. Alternatively, the antibody binds to an epitope that is exposed on the surface of the cell. The antibody is a polyclonal antisera or monoclonal antibody. The invention encompasses not only an intact monoclonal antibody, but also an immunologically-active antibody fragment, e.g., a Fab or (Fab)$_2$ fragment; an engineered single chain Fv molecule; or a chimeric molecule, e.g., an antibody which contains the binding specificity of one antibody, e.g., of murine origin, and the remaining portions of another antibody, e.g., of human origin. Preferably the antibody is a monoclonal antibody such as FB50, 5C7, 5E9, 19B, 48A, 74A, 78A, 86A, HA238A, HA221, HA239, HA241, HA329, or HA355. Antibodies which bind to the same epitopes as those monoclonal antibodies are also within the invention.

An HAAH-specific intrabody is a recombinant single chain HAAH-specific antibody that is expressed inside a target cell, e.g., tumor cell. Such an intrabody binds to endogenous intracellular HAAH and inhibits HAAH enzymatic activity or prevents HAAH from binding to an intracellular ligand. HAAH-specific intrabodies inhibit intracellular signal transduction, and as a result, inhibit growth of tumors which overexpress HAAH.

A kit for diagnosis of a tumor in a mammal contains an HAAH-specific antibody. The diagnostic assay kit is preferentially formulated in a standard two-antibody binding format in which one HAAH-specific antibody captures HAAH in a patient sample and another HAAH-specific antibody is used to detect captured HAAH. For example, the capture antibody is immobilized on a solid phase, e.g., an assay plate, an assay well, a nitrocellulose membrane, a bead, a dipstick, or a component of an elution column. The second antibody, i.e., the detection antibody, is typically tagged with a detectable label such as a colorimetric agent or radioisotope.

Also within the invention is a method of inhibiting tumor growth in a mammal, which is carried out by administering to the mammal a compound which inhibits expression or enzymatic activity of HAAH. Preferably, the compound is substantially pure nucleic acid molecule such as an HAAH antisense DNA, the sequence of which is complementary to a coding sequence of HAAH. Expression of HAAH is inhibited by contacting mammalian cells, e.g., tumor cells, with HAAH antisense DNA or RNA, e.g., a synthetic HAAH antisense oligonucleotide. For example, HAAH antisense nucleic acid is introduced into glioblastoma cells or other tumor cells which overexpress HAAH. Binding of the antisense nucleic acid to an HAAH transcript in the target cell results in a reduction in HAAH production by the cell. By the term "antisense nucleic acid" is meant a nucleic acid (RNA or DNA) which is complementary to a portion of an mRNA, and which hybridizes to and prevents translation of the mRNA. Preferably, the antisense DNA is complementary to the 5' regulatory sequence or the 5' portion of the coding sequence of HAAH mRNA (e.g., a sequence encoding a signal peptide or a sequence within exon 1 of the HAAH gene). Standard techniques of introducing antisense DNA into the cell may be used, including those in which antisense DNA is a template from which an antisense RNA is transcribed. The method is to treat tumors in which expression of HAAH is upregulated, e.g., as a result of malignant transformation of the cells. The length of the oligonucleotide is at least 10 nucleotides and may be as long as the naturally-occurring HAAH transcript. Preferably, the length is between 10 and 50 nucleotides, inclusive. More preferably, the length is between 10 and 20 nucleotides, inclusive.

By "substantially pure DNA or RNA" is meant that the nucleic acid is free of the genes which, in the naturally-occurring genome of the organism from which the DNA of the invention is derived, flank a HAAH gene. The term therefore includes, for example, a recombinant nucleic acid which is incorporated into a vector, into an autonomously replicating plasmid or virus, or into the genomic DNA of a procaryote or eucaryote at a site other than its natural site; or which exists as a separate molecule (e.g., a cDNA or a genomic or cDNA fragment produced by PCR or restriction endonuclease digestion) independent of other sequences. It also includes a recombinant nucleic acid which is part of a hybrid gene encoding additional polypeptide sequence such as a nucleic acid encoding a chimeric polypeptide, e.g., one encoding an antibody fragment linked to a cytotoxic polypeptide. Alternatively, HAAH expression is inhibited by administering a ribozyme or a compound which inhibits binding of Fos or Jun to an HAAH promoter sequence.

Compounds, which inhibit an enzymatic activity of HAAH, are useful to inhibit tumor growth in a mammal. By enzymatic activity of HAAH is meant hydroxylation of an epidermal growth factor (EGF)-like domain of a polypeptide. For example an EGF-like domain has the consensus sequence $CX_7CX_4CX_{10}CXCX_8C$ (SEQ ID NO:1). HAAH hydroxylase activity is inhibited intracellularly. For example, a dominant negative mutant of HAAH (or a nucleic acid encoding such a mutant) is administered. The dominant negative HAAH mutant contains a mutation which changes a ferrous iron binding site from histidine of a naturally-occurring HAAH sequence to a non-iron-binding amino acid, thereby abolishing the hydroxylase activity of HAAH. The histidine to be mutated, e.g., deleted or substituted, is located in the carboxyterminal catalytic domain of HAAH. For example, the mutation is located between amino acids 650–700 (such as the His motif, underlined sequence of SEQ ID NO:2) the native HAAH sequence. For example, the mutation is at residues 671, 675, 679, or 690 of SEQ ID NO:2. An HAAH-specific intrabody is also useful to bind to HAAH and inhibit intracellular HAAH enzymatic activity, e.g., by binding to an epitope in the catalytic domain of HAAH. Other compounds such as L-mimosine or hydroxypyridone are administered directly into a tumor site or systemically to inhibit HAAH hydroxylase activity.

For example, a compound which inhibits HAAH hydroxylation is a polypeptide that binds a HAAH ligand but does not transduce an intracellular signal or an polypeptide which contains a mutation in the catalytic site of HAAH. Such a polypeptide contains an amino acid sequence that is at least 50% identical to a naturally-occurring HAAH amino acid sequence or a fragment thereof and which has the ability to inhibit HAAH hydroxylation of substrates containing an EGF-like repeat sequence. More preferably, the polypeptide contains an amino acid sequence that is at least 75%, more preferably at least 85%, more preferably at least 95% identical to SEQ ID NO:2.

A substantially pure HAAH polypeptide or HAAH-derived polypeptide such as a mutated HAAH polypeptide is preferably obtained by expression of a recombinant nucleic acid encoding the polypeptide or by chemically synthesizing the protein. A polypeptide or protein is substantially pure when it is separated from those contaminants which accompany it in its natural state (proteins and other naturally-occurring organic molecules). Typically, the polypeptide is substantially pure when it constitutes at least 60%, by weight, of the protein in the preparation. Preferably, the protein in the preparation is at least 75%, more preferably at least 90%, and most preferably at least 99%, by weight, HAAH. Purity is measured by any appropriate method, e.g., column chromatography, polyacrylamide gel electrophoresis, or HPLC analysis. Accordingly, substantially pure polypeptides include recombinant polypeptides derived from a eucaryote but produced in *E. coli* or another procaryote, or in a eucaryote other than that from which the polypeptide was originally derived.

Nucleic acid molecules which encode such HAAH or HAAH-derived polypeptides are also within the invention.

TABLE 1

Amino acid sequence of HAAH

| | | | | | | |
|---|---|---|---|---|---|---|
| MAQRKNAKSS | GNSSSSGSGS | GSTSAGSSSP | GARRETKHGG | HKNGRKGGLS | GTSFFTWFMV | 61 |
| IALLGVWTSV | AVVWFDLVDY | EEVLGKLGIY | DADGDGDFDV | DDAKVLLGLK | ERSTSEPAVP | 121 |
| PEEAEPHTEP | EEQVPVEAEP | QNIEDEAKEQ | IQSLLHEMVH | AEHVEGEDLQ | QEDGPTGEPQ | 181 |
| QEDDEFLMAT | DVDDRFETLE | PEVSHEETEH | SYHVEETVSQ | DCNQDMEEMM | SEQENPDSSE | 241 |
| PVVEDERLHH | DTDDVTYQVY | EEQAVYEPLE | NEGIEITEVT | APPEDNPVED | SQVIVEEVSI | 301 |
| FPVEEQQEVP | PETNRKTDDP | EQKAKVKKKK | PKLLNKFDKT | IKAELDAAEK | LRKRGKIEEA | 361 |
| VNAFKELVRK | YPQSPRARYG | KAQCEDDLAE | KRRSNEVLRG | AIETYQEVAS | LPDVPADLLK | 421 |
| LSLKRRSDRQ | QFLGHMRGSL | LTLQRLVQLF | PNDTSLKNDL | GVGYLLIGDN | DNAKKVYEEV | 481 |
| LSVTPNDGFA | KVHYGFILKA | QNKIAESIPY | LKEGIESGDP | GTDDGRFYFH | LGDAMQRVGN | 541 |
| KEAYKWYELG | HKRGHFASVW | QRSLYNVNGL | KAQPWWTPKE | TGYTELVKSL | ERNWKLIRDE | 601 |
| GLAVMDKAKG | LFLPEDENLR | EKGDWSQFTL | WQQGRRNENA | CKGAPKTCTL | LEKFPETTGC | 661 |
| RRGQIKYSIM | HPGTHVWPHT | GPTNCRLRMH | LGLVIPKEGC | KIRCANETRT | WEEGKVLIFD | 721 |
| DSFEHEVWQD | ASSFRLIFIV | DVWHPELTPQ | QRRSLPAI | | | |

(SEQ ID NO:2; GENBANK Accession No. S83325; His motif is underlined; conserved sequences within the catalytic domain are designated by bold type)

TABLE 2

HAAH cDNA sequence

| | |
|---|---|
| cggaccgtgc aatggcccag cgtaagaatg ccaagaqcag cggcaacagc agcagcagcg | 61 |
| gctccggcag cggtagcacg agtgcgggca gcagcagccc cggggcccgg agagagacaa | 121 |
| agcatggagg acacaagaat gggaggaaag gcggactctc gggaacttca ttcttcacgt | 181 |
| ggtttatggt gattgcattg ctgggcgtct ggacatctgt agctgtcgtt tggtttgatc | 241 |
| ttgttgacta tgaggaagtt ctaggaaaac taggaatcta tgatgctgat ggtgatggag | 301 |
| attttgatgt ggatgatgcc aaagttttat taggacttaa agagagatct acttcagagc | 361 |
| cagcagtccc gccagaagag gctgagccac acactgagcc cgaggagcag gttcctgtgg | 421 |
| aggcagaacc ccagaatatc gaagatgaag caaaagaaca aattcagtcc cttctccatg | 481 |
| aaatggtaca cgcagaacat gttgagggag aagacttgca acaagaagat ggacccacag | 541 |
| gagaaccaca acaagaggat gatgagtttc ttatggcgac tgatgtagat gatagatttg | 601 |
| agaccctgga acctgaagta tctcatgaag aaaccgagca tagttaccac gtggaagaga | 661 |
| cagtttcaca agactgtaat caggatatgg aagagatgat gtctgagcag gaaaatccag | 721 |
| attccagtga accagtagta gaagatgaaa gattgcacca tgatacagat gatgtaacat | 781 |
| accaagtcta tgaggaacaa gcagtatatg aacctctaga aaatgaaggg atagaaatca | 841 |
| cagaagtaac tgctccccct gaggataatc ctgtagaaga ttcacaggta attgtagaag | 901 |
| aagtaagcat ttttcctgtg gaagaacagc aggaagtacc accagaaaca aatagaaaaa | 961 |
| cagatgatcc agaacaaaaa gcaaagtta agaaaagaa gcctaaactt ttaaataaat | 1021 |
| ttgataagac tattaaagct gaacttgatg ctgcagaaaa actccgtaaa aggggaaaaa | 1081 |
| ttgaggaagc agtgaatgca tttaaagaac tagtacgcaa ataccctcag agtccacgag | 1141 |
| caagatatgg gaaggcgcag tgtgaggatg atttggctga aagaggaga agtaatgagg | 1201 |
| tgctacgtgg agccatcgag acctaccaag aggtggccag cctacctgat gtccctgcag | 1261 |
| acctgctgaa gctgagtttg aagcgtcgct cagacaggca acaatttcta ggtcatatga | 1321 |
| gaggttccct gcttaccctg cagagattag ttcaactatt tcccaatgat acttccttaa | 1381 |
| aaaatgacct tggcgtggga tacctcttga taggagataa tgacaatgca aagaaagttt | 1441 |
| atgaagaggt gctgagtgtg acacctaatg atggctttgc taaagtccat tatggcttca | 1501 |
| tcctgaaggc acagaacaaa attgctgaga gcatcccata tttaaaggaa ggaatagaat | 1561 |
| ccggagatcc tggcactgat gatgggagat tttatttcca cctgggggat gccatgcaga | 1621 |
| gggttgggaa caaagaggca tataagtggt atgagcttgg gcacaagaga ggacactttg | 1681 |
| catctgtctg gcaacgctca ctctacaatg tgaatggact gaaagcacag ccttggtgga | 1741 |
| ccccaaaaga aacgggctac acagagttag taaagtcttt agaaagaaac tggaagttaa | 1801 |
| tccgagatga aggccttgca gtgatggata agccaaagg tctcttcctg cctgaggatg | 1861 |
| aaaacctgag ggaaaaaggg gactggagcc agttcacgct gtggcagcaa ggaagaagaa | 1921 |
| atgaaaatgc ctgcaaagga gctcctaaaa cctgtacctt actagaaaag ttccccgaga | 1981 |
| caacaggatg cagaagagga cagatcaaat attccatcat gcaccccggg actcacgtgt | 2041 |
| ggccgcacac agggcccaca aactgcaggc tccgaatgca cctgggcttg gtgattccca | 2101 |
| aggaaggctg caagattcga tgtgccaacg agaccaggac ctgggaggaa ggcaaggtgc | 2161 |
| tcatctttga tgactccttt gagcacgagg tatggcagga tgcctcatct ttccggctga | 2221 |

TABLE 2-continued

HAAH cDNA sequence tattcatcgt ggatgtgtgg catccggaac tgacaccaca gcagagacgc agccttccag    2281
caatttagca tgaattcatg caagcttggg aaactctgga gaga (SEQ ID NO:3 ; GENBANK Accession No. S83325; codon encoding initiating methionine is underlined).

Methods of inhibiting tumor growth also include administering a compound which inhibits HAAH hydroxylation of a NOTCH polypeptide. For example, the compound inhibits hydroxylation of an EGF-like cysteine-rich repeat sequence in a NOTCH polypeptide, e.g., one containing the consensus sequence CDXXXCXXKXGNGXCDXXCN-NAACXXDGXDC (SEQ ID NO:4). Polypeptides containing an EGF-like cysteine-rich repeat sequence are administered to block hydroxylation of endogenous NOTCH.

Growth of a tumor which overexpresses HAAH is also inhibited by administering a compound which inhibits signal transduction through the insulin receptor substrate (IRS) signal transduction pathway. Preferably the compound inhibits IRS phosphorylation. For example, the compound is a peptide or non-peptide compound which binds to and inhibits phosphorylation at residues 46, 465, 551, 612, 632, 662, 732, 941, 989, or 1012 of SEQ ID NO:5. Compounds include polypeptides such those which block an IRS phosphorylation site such as a Glu/Tyr site. Antibodies such as those which bind to a carboxyterminal domain of IRS containing a phosphorylation site block IRS phosphorylation, and as a consequence, signal transduction along the pathway. Inhibition of IRS phosphorylation in turn leads to inhibition of cell proliferation. Other compounds which inhibit IRS phosphorylation include vitamin D analogue EB1089 and Wortmannin.

HAAH-overproducing tumor cells were shown to express HAAH both intracellularly and on the surface of the tumor cell. Accordingly, a method of killing a tumor cell is carried out by contacting such a tumor cell with a cytotoxic agent linked to an HAAH-specific antibody. The HAAH-specific antibody (antibody fragment, or ligand which binds to extracellular HAAH) directs the chimeric polypeptide to the surface of the tumor cell allowing the cytotoxic agent to damage or kill the tumor cell to which the antibody is bound. The monoclonal antibody binds to an epitope of HAAH such as an epitope exposed on the surface of the cell or in the catalytic site of HAAH. The cytotoxic composition preferentially kills tumor cells compared to non-tumor cell.

Screening methods to identify anti-tumor agents which inhibit the growth of tumors which overexpress HAAH are also within the invention. A screening method used to determine whether a candidate compound inhibits HAAH enzymatic activity includes the following steps: (a) providing a HAAH polypeptide, e.g., a polypeptide which contains the carboxyterminal catalytic site of HAAH; (b) providing a polypeptide comprising an EGF-like domain; (c) contacting the HAAH polypeptide or the EGF-like polypeptide with the candidate compound; and (d) determining hydroxylation of the EGF-like polypeptide of step (b). A decrease in hydroxylation in the presence of the candidate compound compared to that in the absence of said compound indicates that the compound inhibits HAAH hydroxylation of EGF-like domains in proteins such as NOTCH.

Anti-tumor agents which inhibit HAAH activation of NOTCH are identified by (a) providing a cell expressing HAAH; (b) contacting the cell with a candidate compound; and (c) measuring translocation of activated NOTCH to the nucleus of said cell. Translocation is measured by using a reagent such as an antibody which binds to a 110 kDa activation fragment of NOTCH. A decrease in translocation in the presence of the candidate compound compared to that in the absence of the compound indicates that the compound inhibits HAAH activation of NOTCH, thereby inhibiting NOTCH-mediated signal transduction and proliferation of HAAH-overexpressing tumor cells.

Nucleotide and amino acid comparisons described herein were carried out using the Lasergene software package (DNASTAR, Inc., Madison, Wis.). The MegAlign module used was the Clustal V method (Higgins et al., 1989, CABIOS 5(2):151–153). The parameter used were gap penalty 10, gap length penalty 10.

Hybridization is carried out using standard techniques, such as those described in Ausubel et al. (*Current Protocols in Molecular Biology*, John Wiley & Sons, 1989). "High stringency" refers to nucleic acid hybridization and wash conditions characterized by high temperature and low salt concentration, e.g., wash conditions of 65° C. at a salt concentration of 0.1×SSC. "Low" to "moderate" stringency refers to DNA hybridization and wash conditions characterized by low temperature and high salt concentration, e.g., wash conditions of less than 60° C. at a salt concentration of at least 1.0×SSC. For example, high stringency conditions include hybridization at 42° C. in the presence of 50% formamide; a first wash at 65° C. in the presence of 2×SSC and 1% SDS; followed by a second wash at 65° C. in the presence of 0.1%×SSC. Lower stringency conditions suitable for detecting DNA sequences having about 50% sequence identity to an HAAH gene sequence are detected by, for example, hybridization at about 42° C. in the absence of formamide; a first wash at 42° C., 6×SSC, and 1% SDS; and a second wash at 50° C., 6×SSC, and 1% SDS.

Other features and advantages of the invention will be apparent from the following description of the preferred embodiments thereof, and from the claims.

BRIEF DESCRIPTION OF THE DRAWINGS

FIG. 3A shows a measurement of murine AAH enzymatic activity in clones 7, 16 and 18, and FIG. 3B shows colony formation exhibited by clones 7, 16 and 18. Data is presented as mean number of colonies 10 days after plating ±SEM. All three clones with modest increases in HAAH enzymatic activity, that correlated with protein expression, exhibited anchorage independent growth.

FIG. 5C) to induce neurite outgrowth as occurs during tumor cell invasion. The cells were treated with 10 μM retinoic acid or 100 nM PMA for 0, 1, 2, 3, 4, or 7 days. Cell lysates were analyzed by Western blot analysis using an HAAH-specific monoclonal antibody to detect the 85 kDa AAH protein. The levels of immunoreactivity were measured by volume densitometry (arbitrary units). The graphs indicate the mean ±S.D. of results obtained from three separate experiments. In FIG. 5D, PNET2 cells were treated for 24 hours with sub-lethal concentrations of $H_2O_2$ to induce neurite retraction. Viability of greater than 90% of the cells was demonstrated by Trypan blue dye exclusion. Similar results were obtained for SH-Sy5y cells.

DETAILED DESCRIPTION

Figure 1:
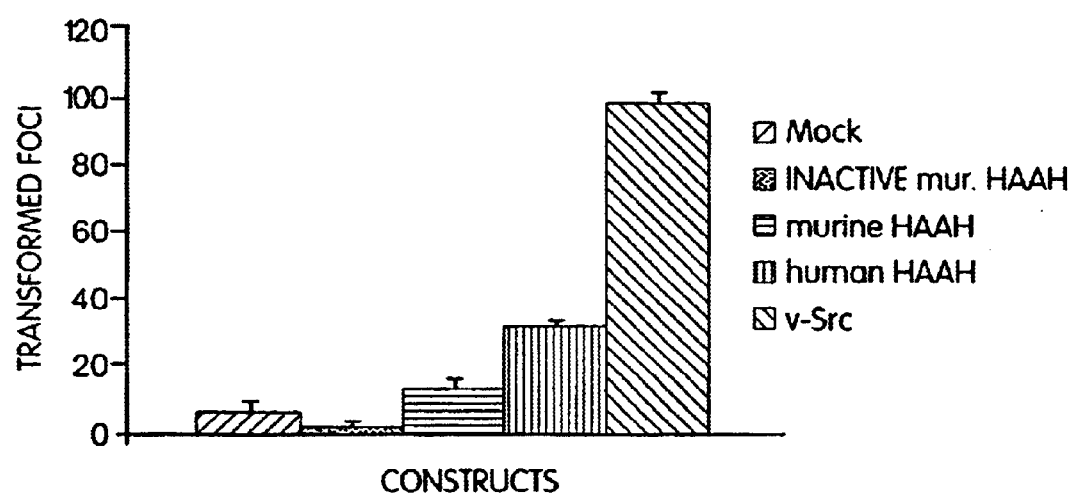
FIG. 1 is a bar graph showing colony formation induced by transient transfection of NIH-3T3 cells with various AAH cDNAs. Colony formation was induced by transient transfection with 10 μg DNA. In contrast, the mutant murine AAH construct without enzymatic activity has no transforming activity. The data is presented as mean number of transformed foci ±SEM.

HAAH is a protein belonging to the (α-ketoglutarate dependent dioxygenase family of prolyl and lysyl hydroxylases which play a key role in collagen biosynthesis. This molecule hydroxylates aspartic acid or asparagine residues in EGF-like domains of several proteins in the presence of ferrous iron. These EGF-like domains contain conserved motifs, that form repetitive sequences in proteins such as clotting factors, extracellular matrix proteins, LDL receptor, NOTCH homologues or NOTCH ligand homologues.

The alpha-ketoglutarate-dependent dioxygenase aspartyl (asparaginyl) beta-hydroxylase (AAH) specifically hydroxylates one aspartic or asparagine residue in EGF-like domains of various proteins. The 4.3-kb cDNA encoding the human AspH (hAspH) hybridizes with 2.6 kb and 4.3 kb transcripts in transformed cells, and the deduced amino acid sequence of the larger transcript encodes an protein of about 85 kDa. Both in vitro transcription and translation and Western blot analysis also demonstrate a 56-kDa protein that may result from posttranslational cleavage of the catalytic C terminus.

An physiological function of AAH is the post-translational beta-hydroxylation of aspartic acid in vitamin K-dependent coagulation proteins. However, the abundant expression of AAH in several malignant neoplasms, and low levels of AAH in many normal cells indicate a role for this enzyme in malignancy. The AAH gene is also highly expressed in cytotrophoblasts, but not syncytiotrophoblasts of the placenta. Cytotrophoblasts are invasive cells that mediate placental implantation. The increased levels of AAH expression in human cholangiocarcinomas, hepatocellular carcinomas, colon cancers, and breast carcinomas were primarily associated with invasive or metastatic lesions. Moreover, overexpression of AAH does not strictly reflect increased DNA synthesis and cellular proliferation since high levels of AAH immunoreactivity were observed in 100 percent of cholangiocarcinomas, but not in human or experimental disease processes associated with regeneration or nonneoplastic proliferation of bile ducts. AAH overexpression and attendant high levels of beta hydroxylase activity lead to invasive growth of transformed neoplastic cells. Detection of an increase in HAAH expression is useful for early and reliable diagnosis of the cancer types which have now been characterized as overexpressing this gene product.

Diagnosis of Malignant Tumors

HAAH is overexpressed in many tumors of endodermal origin and in at least 95% of CNS tumors compared to normal noncancerous cells. An increase in HAAH gene product in a patient-derived tissue sample (e.g., solid tissue or bodily fluid) is carried out using standard methods, e.g., by Western blot assays or a quantitative assay such as ELISA. For example, a standard competitive ELISA format using an HAAH-specific antibody is used to quantify patient HAAH levels. Alternatively, a sandwich ELISA using a first antibody as the capture antibody and a second HAAH-specific antibody as a detection antibody is used.

Methods of detecting HAAH include contacting a component of a bodily fluid with an HAAH-specific antibody bound to solid matrix, e.g., microtiter plate, bead, dipstick. For example, the solid matrix is dipped into a patient-derived sample of a bodily fluid, washed, and the solid matrix is contacted with a reagent to detect the presence of immune complexes present on the solid matrix.

Proteins in a test sample are immobilized on (bound to) a solid matrix. Methods and means for covalently or noncovalently binding proteins to solid matrices are known in the art. The nature of the solid surface may vary depending upon the assay format. For assays carried out in microtiter wells, the solid surface is the wall of the well or cup. For assays using beads, the solid surface is the surface of the bead. In assays using a dipstick (i.e., a solid body made from a porous or fibrous material such as fabric or paper) the surface is the surface of the material from which the dipstick is made.

Examples of useful solid supports include nitrocellulose (e.g., in membrane or microtiter well form), polyvinyl chloride (e.g., in sheets or microtiter wells), polystyrene latex (e.g., in beads or microtiter plates, polyvinylidine fluoride (known as IMMULON™), diazotized paper, nylon membranes, activated beads, and Protein A beads. The solid support containing the antibody is typically washed after contacting it with the test sample, and prior to detection of bound immune complexes. Incubation of the antibody with the test sample is followed by detection of immune complexes by a detectable label. For example, the label is enzymatic, fluorescent, chemiluminescent, radioactive, or a dye. Assays which amplify the signals from the immune complex are also known in the art, e.g., assays which utilize biotin and avidin.

An HAAH-detection reagent, e.g., an antibody, is packaged in the form of a kit, which contains one or more HAAH-specific antibodies, control formulations (positive and/or negative), and/or a detectable label. The assay may be in the form of a standard two-antibody sandwich assay format known in the art.

Production of HAAH-specific Antibodies

Anti-HAAH antibodies were obtained by techniques well known in the art. Such antibodies are polyclonal or monoclonal. Polyclonal antibodies were obtained, for example, by the methods described in Ghose et al., Methods in Enzymology, Vol. 93, 326–327, 1983. An HAAH polypeptide, or an antigenic fragment thereof, was used as the immunogen to stimulate the production of polyclonal antibodies in the antisera of rabbits, goats, sheep, or rodents. Antigenic polypeptides for production of both polyclonal and monoclonal antibodies useful as immunogens include polypeptides which contain an HAAH catalytic domain. For example, the immunogenic polypeptide is the full-length mature HAAH protein or an HAAH fragment containing the carboxyterminal catalytic domain e.g., an HAAH polypeptide containing the His motif of SEQ ID NO:2.

Antibodies which bind to the same epitopes as those antibodies disclosed herein as identified using standard methods, e.g., competitive binding assays, known in the art.

Monoclonal antibodies were obtained by standard techniques. Ten µg of purified recombinant HAAH polypeptide was administered to mice intraperitoneally in complete Freund's adjuvant, followed by a single boost intravenously (into the tail vein) 3–5 months after the initial inoculation. Antibody-producing hybridomas were made using standard methods. To identify those hybridomas producing antibodies that are highly specific for an HAAH polypeptide, hybridomas were screened using the same polypeptide immunogen used to immunize. Those antibodies which were identified as having HAAH-binding activity are also screened for the ability to inhibit HAAH catalytic activity using the enzymatic assays described below. Preferably, the antibody has a binding affinity of at least about $10^8$ liters/mole and more preferably, an affinity of at least about $10^9$ liters/mole.

Monoclonal antibodies are humanized by methods known in the art, e.g., MAbs with a desired binding specificity can be commercially humanized (Scotgene, Scotland; Oxford Molecular, Palo Alto, Calif.).

HAAH-specific intrabodies are produced as follows. Following identification of a hybridoma producing a suitable monoclonal antibody, DNA encoding the antibody is cloned. DNA encoding a single chain HAAH-specific antibody in which heavy and light chain variable domains are separated by a flexible linker peptide is cloned into an expression vector using known methods (e.g., Marasco et al., 1993, Proc. Natl. Acad. Sci. USA 90:7889-7893 and Marasco et al., 1997, Gene Therapy 4:11-15). Such constructs are introduced into cells, e.g., using standard gene delivery techniques for intracellular production of the antibodies. Intracellular antibodies, i.e., intrabodies, are used to inhibit signal transduction by HAAH. Intrabodies which bind to a carboxyterminal catalytic domain of HAAH inhibit the ability of HAAH to hydroxylate EGF-like target sequences.

Methods of linking HAAH-specific antibodies (or fragments thereof) which bind to cell surface exposed epitopes of HAAH on the surface of a tumor cell are linked to known cytotoxic agents, e.g., ricin or diptheria toxin, using known methods.

Deposit of Biological Materials

Under the terms of the Budapest Treaty on the International Recognition of the Deposit of Microorganisms for the Purpose of Patent Procedure, hybridoma FB501 (which produces monoclonal antibody FB50; designated ATCC accession no. PTA 3386), hybridoma HA386A (which produces monoclonal antibody 86A; designated ATCC accession no. 3385), hybridoma HA15C7A (which produces monoclonal antibody 5C7; designated ATCC accession no. 3383), and hybridoma HA219B (which produces monoclonal antibody 19B; designated ATCC accession no. 3384) were deposited on May 17, 2001, with the American Type Culture Collection (ATCC) of 10801 University Boulevard, Manassas, Va. 20110-2209 USA.

Applicants' assignee represents that the ATCC is a depository affording permanence of the deposit and ready accessibility thereto by the public if a patent is granted. All restrictions on the availability to the public of the material so deposited will be irrevocably removed upon the granting of a patent. The material will be available during the pendency of the patent application to one determined by the Commissioner to be entitled thereto under 37 CFR 1.14 and 35 U.S.C. 122. The deposited material will be maintained with all the care necessary to keep it viable and uncontaminated for a period of at least five years after the most recent request for the furnishing of a sample of the deposited plasmid, and in any case, for a period of at least thirty (30) years after the date of deposit or for the enforceable life of the patent, whichever period is longer. Applicant's assignee acknowledges its duty to replace the deposit should the depository be unable to furnish a sample when requested due to the condition of the deposit.

Methods of Treating Malignant Tumors

Patients with tumors characterized as overexpressing HAAH as such tumors of endodermal origin or CNS tumors are treated by administering HAAH antisense nucleic acids.

Antisense therapy is used to inhibit expression of HAAH in patients suffering from hepatocellular carcinomas, cholangiocarcinomas, glioblastomas and neuroblastomas. For example, an HAAH antisense strand (either RNA or DNA) is directly introduced into the cells in a form that is capable of binding to the mRNA transcripts. Alternatively, a vector containing a sequence which, which once within the target cells, is transcribed into the appropriate antisense mRNA, may be administered. Antisense nucleic acids which hybridize to target mRNA decrease or inhibit production of the polypeptide product encoded by a gene by associating with the normally single-stranded mRNA transcript, thereby interfering with translation and thus, expression of the protein. For example, DNA containing a promoter, e.g., a tissue-specific or tumor specific promoter, is operably linked to a DNA sequence (an antisense template), which is transcribed into an antisense RNA. By "operably linked" is meant that a coding sequence and a regulatory sequence(s) (i.e., a promoter) are connected in such a way as to permit gene expression when the appropriate molecules (e.g., transcriptional activator proteins) are bound to the regulatory sequence(s).

Oligonucleotides complementary to various portions of HAAH mRNA are tested in vitro for their ability to decrease production of HAAH in tumor cells (e.g., using the FOCUS hepatocellular carcinoma (HCC) cell line) according to standard methods. A reduction in HAAH gene product in cells contacted with the candidate antisense composition compared to cells cultured in the absence of the candidate composition is detected using HAAH-specific antibodies or other detection strategies. Sequences which decrease production of HAAH in in vitro cell-based or cell-free assays are then be tested in vivo in rats or mice to confirm decreased HAAH production in animals with malignant neoplasms.

Antisense therapy is carried out by administering to a patient an antisense nucleic acid by standard vectors and/or gene delivery systems. Suitable gene delivery systems may include liposomes, receptor-mediated delivery systems, naked DNA, and viral vectors such as herpes viruses, retroviruses, adenoviruses and adeno-associated viruses, among others. A reduction in HAAH production results in a decrease in signal transduction via the IRS signal transduction pathway. A therapeutic nucleic acid composition is formulated in a pharmaceutically acceptable carrier. The therapeutic composition may also include a gene delivery system as described above. Pharmaceutically acceptable carriers are biologically compatible vehicles which are suitable for administration to an animal: e.g., physiological saline. A therapeutically effective amount of a compound is an amount which is capable of producing a medically desirable result such as reduced production of an HAAH gene product or a reduction in tumor growth in a treated animal.

Parenteral administration, such as intravenous, subcutaneous, intramuscular, and intraperitoneal delivery routes, may be used to deliver nucleic acids or HAAH-inhibitory peptides or non-peptide compounds. For treatment of CNS tumors, direct infusion into cerebrospinal fluid is useful. The blood-brain barrier may be compromised in cancer patients, allowing systemically administered drugs to pass through the barrier into the CNS. Liposome formulations of therapeutic compounds may also facilitate passage across the blood-brain barrier.

Dosages for any one patient depends upon many factors, including the patient's size, body surface area, age, the particular nucleic acid to be administered, sex, time and route of administration, general health, and other drugs being administered concurrently. Dosage for intravenous administration of nucleic acids is from approximately $10^6$ to $10^{22}$ copies of the nucleic acid molecule.

Ribozyme therapy is also be used to inhibit HAAH gene expression in cancer patients. Ribozymes bind to specific mRNA and then cut it at a predetermined cleavage point, thereby destroying the transcript. These RNA molecules are used to inhibit expression of the HAAH gene according to methods known in the art (Sullivan et al., 1994, J. Invest. Derm. 103:85S–89S; Czubayko et al., 1994, J. Biol. Chem. 269:21358–21363; Mahieu et al., 1994, Blood 84:3758–65; Kobayashi et al. 1994, Cancer Res. 54:1271–1275).

Methods of Identifying Compounds that Inhibit HAAH Enzymatic Activity

Aspartyl (asparaginyl) beta-hydroxylaseydroxylase (AAH) activity is measured in vitro or in vivo. For example, HAAH catalyzes posttranslational modification of β carbon of aspartyl and asparaginyl residues of EGF-like polypeptide domains. An assay to identify compounds which inhibit hydroxylase activity is carried out by comparing the level of hydroxylation in an enzymatic reaction in which the candidate compound is present compared to a parallel reaction in the absence of the compound (or a predetermined control value). Standard hydroxylase assays carried out in a testtube are known in the art, e.g., Lavaissiere et al., 1996, J. Clin. Invest. 98:1313–1323; Jia et al., 1992, J. Biol. Chem. 267:14322–14327; Wang et al., 1991, J. Biol. Chem. 266:14004–14010; or Gronke et al., 1990, J. Biol. Chem. 265:8558–8565. Hydroxylase activity is also measured using carbon dioxide ($^{14}CO_2$ capture assay) in a 96-well microtiter plate format (Zhang et al., 1999, Anal. Biochem. 271:137–142. These assays are readily automated and suitable for high throughput screening of candidate compounds to identify those with hydroxylase inhibitory activity.

Candidate compound which inhibit HAAH activation of NOTCH are identified by detecting a reduction in activated NOTCH in a cell which expresses or overexpresses HAAH, e.g., FOCUS HCC cells. The cells are cultured in the presence of a candidate compound. Parallel cultures are incubated in the absence of the candidate compound. To evaluate whether the compound inhibits HAAH activation of NOTCH, translocation of activated NOTCH to the nucleus of the cell is measured. Translocation is measured by detecting a 110 kDa activation fragment of NOTCH in the nucleus of the cell. The activation fragment is cleaved from the large (approximately 300 kDa) transmembrane NOTCH protein upon activation. Methods of measuring NOTCH translocation are known, e.g, those described by Song et al., 1999, Proc. Natl. Acad. Sci U.S.A. 96:6959–6963 or Capobianco et al., 1997, Mol. Cell Biol. 17:6265–6273. A decrease in translocation in the presence of the candidate compound compared to that in the absence of the compound indicates that the compound inhibits HAAH activation of NOTCH, thereby inhibiting NOTCH-mediated signal transduction and proliferation of HAAH-overexpressing tumor cells.

Methods of screening for compounds which inhibit phosphorylation of IRS are carried out by incubating IRS-expressing cells in the presence and absence of a candidate compound and evaluating the level of IRS phosphorylation in the cells. A decrease in phosphorylation in cells cultured in the presence of the compound compared to in the absence of the compound indicates that the compound inhibits IRS-1 phosphorylation, and as a result, growth of HAAH-overexpressing tumors. Alternatively, such compounds are identified in an in vitro phosphorylation assay known in the art, e.g., one which measured phosphorylation of a synthetic substrate such as poly (Glu/Tyr).

EXAMPLE 1

Increased Expression of HAAH is Associated with Malignant Transformation

HAAH is a highly conserved enzyme that hydroxylates EGF-like domains in transformation associated proteins. The HAAH gene is overexpressed in human hepatocellular carcinomas and cholangiocarcinomas. HAAH gene expression was found to be undetectable during bile duct proliferation in both human disease and rat models compared to cholangiocarcinoma. Overexpression of HAAH in NIH-3T3 cells was associated with generation of a malignant phenotype, and enzymatic activity was found to be required for cellular transformation. The data described below indicate that overexpression of HAAH is linked to cellular transformation of biliary epithelial cells.

To identify molecules that are specifically overexpressed in transformed malignant cells of human hepatocyte origin, the FOCUS hepatocellular carcinoma (HCC) cell line was used as an immunogen to generate monoclonal antibodies (mAb) that specifically or preferentially recognize proteins associated with the malignant phenotype. A lambda GT11 cDNA expression library derived from HepG2 HCC cells was screened, and HAAH-specific mAb produced against the FOCUS cell line was found to recognize an epitope on a protein encoded by an HAAH cDNA. The HAAH enzyme was found to be upregulated in several different human transformed cell lines and tumor tissues compared to adjacent human tissue counterparts. The overexpressed HAAH enzyme in different human malignant tissues was found to be catalytically active.

HAAH gene expression was examined in proliferating bile ducts and in NIH 3T3 cells. Its role in the generation of the malignant phenotype was measured by the formation of transformed foci, growth in soft agar as an index of anchorage independent growth and tumor formation in nude mice. The role of enzymatic activity in the induction of transformed phenotype was measured by using a cDNA construct with a mutation in the catalytic site that abolished hydroxylase activity. The results indicated that an increase in expression of HAAH gene is associated with malignant transformation of bile ducts.

The following materials and methods were used to generate the data described below.

Antibodies

The FB50 monoclonal antibody was generated by cellular immunization of Balb/C mice with FOCUS HCC cells. A monoclonal anti-Dengue virus antibody was used as a non-relevant control. The HBOH2 monoclonal antibody was generated against a 52 kDa recombinant HAAH polypeptide and recognizes the catalytic domain of beta-hydroxylase from mouse and human proteins. Polyclonal anti-HAAH antibodies cross-react with rat hydroxylase protein. Control antibody anti-Erk-1 was purchased from Santa Cruz Biotechnology, Inc, CA. Sheep anti-mouse and donkey anti-rabbit antisera labeled with horseradish peroxidase were obtained from Amersham, Arlington Heights, Ill.

Constructs

The murine full length AAH construct (pNH376) and the site-directed mutation construct (pNH376-H660) with abolished catalytic activity were cloned into the eukaryotic expression vector pcDNA3 (Invitrogen Corp., San Diego, Calif.). The full length human AAH was cloned into prokaryotic expression vector pBC-SK+ (Stratagene, La Jolla, Calif.). The full length human AAH (GENBANK Accession No. S83325) was subcloned into the EcoRI site of the pcDNA3 vector.

Animal Model of Bile Duct Proliferation

Rats were divided into 9 separate groups of 3 animals each except for group 9 which contained 5 rats. Group 1 was the non-surgical control group, and group 2 was the sham-operated surgical control. The remaining groups underwent common bile duct ligation to induce intrahepatic bile duct proliferation and were evaluated at 6, 12, 24, 48 hours and 4, 8 and 16 days as shown in Table 3. Animals were asphyxiated with $CO_2$, and liver samples were taken from left lateral and median lobes, fixed in 2% paraformaldehyde and embedded in paraffin. Liver samples (5 $\mu$m) were cut and stained with hematoxylin and eosin to evaluate intrahepatic bile duct proliferation. Immunohistochemistry was performed with polyclonal anti-HAAH antibodies that cross-react with the rat protein to determine levels of protein expression.

Bile Duct Proliferation Associated with Primary Sclerosing Cholangitis (PSC)

Liver biopsy samples were obtained from 7 individuals with PSC and associated bile duct proliferation. These individuals were evaluated according to standard gastroenterohepatological protocols. Patients were 22–46 years of age and consisted of 4 males and 3 females. Four had associated inflammatory bowel disease (3 ulcerative colitis and 1 Crohn's colitis). All patients underwent a radiological evaluation including abdominal ultrasonography and endoscopic retrograde cholangiopancreaticography to exclude the diagnosis of extrahepatic biliary obstruction. Tissue sections were prepared from paraffin embedded blocks and were evaluated by hematoxylin and eosin staining for bile duct proliferation. Expression of HAAH was determined by immunohistochemistry using an HAAH-specific monoclonal antibody such as FB50.

Immunohistochemistry

Liver tissue sections (5 $\mu$m) were deparaffinized in xylene and rehydrated in graded alcohol. Endogenous peroxidase activity was quenched by a 30-minute treatment with 0.6% $H_2O_2$ in 60% methanol. Endogenous biotin was masked by incubation with avidin-biotin blocking solutions (Vector Laboratories, Burlingame, Calif.). The FB50 mAb (for PSC samples) and polyclonal anti-HAAH-hydroxylase antibodies (for rat liver samples) were added to slides in a humidified chamber at 4° C. overnight. Immunohistochemical staining was performed using a standard avidin-biotin horseradish peroxidase complex (ABC) method using Vectastain Kits with diaminobenzidine (DAB) as the chromogen according to manufacturer's instructions (Vector Laboratories, Inc., Burlingame, Calif.). Tissue sections were counterstained with hematoxylin, followed by dehydration in ethanol. Sections were examined by a light microscopy for bile duct proliferation and HAAH protein expression. Paraffin sections of cholangiocarcinoma and placenta were used as positive controls, and hepatosteatosis samples were used as a negative controls. To control for antibody binding specificity, adjacent sections were immunostained in the absence of a primary antibody, or using non-relevant antibody to Dengue virus. As a positive control for tissue immunoreactivity, adjacent sections of all specimens were immunostained with monoclonal antibody to glyceraldehyde 3-phosphate dehydrogenase.

Western Blot Analysis

Cell lysates were prepared in a standard radioimmunoprecipitation assay (RIPA) buffer containing protease inhibitors. The total amount of protein in the lysates was determined by Bio-Rad colorimetric assay (Bio Rad, Hercules, Calif.) followed by 10% sodium dodecyl sulphate-polyacrylamide gel electrophoresis (SDS-PAGE), transferred to PVDF membranes, and subjected to Western blot analysis using FB50, HBOH2, anti-Erk-1 (used as an internal control for protein loading) as primary, sheep anti-mouse and donkey anti-rabbit antisera labeled with horseradish peroxidase as secondary antibodies. Antibody binding was detected with enhanced chemiluminescence reagents (SuperSignal, Pierce Chemical Company, Rockford, Ill.) and film autoradiography. The levels of immunoreactivity were measured by volume densitometry using NIH Image software.

Enzymatic Activity Assay

AAH activity was measured in cell lysates using the first EGF-like domain of bovine protein S as substrate where $^{14}C$-labeled α-ketogluterate hydroxylates the domain releasing $^{14}C$ containing CO2 according to standard methods, e.g., those described by Jia et al., 1992, J. Biol. Chem. 267:14322–14327; Wang et al., 1991, J. Biol. Chem. 266:14004–14010; or Gronke et al., 1990, J. Biol. Chem. 265:8558–8565. Incubations were carried out at 37° C. for 30 min in a final volume of 40 $\mu$l containing 48 $\mu$g of crude cell extract protein and 75 $\mu$M EGF substrate.

Cell Transfection Studies

The NIH-3T3 cells were cultured in Dulbecco's modified Eagle's medium (DMEM; Mediatech, Washington, D.C.) supplemented with 10% heat-inactivated fetal calf serum (FCS; Sigma Chemical Co., St.Louis, Mo.), 1% L-glutamine, 1% non-essential amino acids and 1% penicillin-streptomycin (GIBCO BRL, Life Technologies, Inc., Grand Island, N.Y.). Subconfluent NIH-3T3 cells ($3 \times 10^5$ cells/60-mm dish) were transfected with 10 µg of one of the following plasmids: 1) non-recombinant pcDNA3 vector (Invitrogen Corp., San Diego, Calif.) as a negative control; 2) pNH376-H660, the murine AAH cDNA that was mutated in the catalytic domain and cloned into the pcDNA3 vector driven by a CMV promoter; 3) pNH376, the wild type murine AAH cDNA cloned into the pcDNA3 vector; 4) pCDHH, wild type human AAH cDNA cloned into the pcDNA3 vector; or 5) pLNCX-UP1, a cDNA that encodes v-Src oncogene (positive control). Cells were transfected using the calcium phosphate transfection kit according to manufacturer's instructions (5 Prime—3 Prime, Inc., Boulder, Colo.). Comparison of cellular transfection efficiency was assessed with the various constructs. For this procedure, confluent plates obtained 48 hours after transfection were split and reseeded into 12 separate 6-cm dishes, and 6 of them were made to grow in the presence of 400 µg/ml G-418 (GIBCO BRL, Life Technologies, Inc., Grant Island, N.Y.) containing medium. The number of G-418 resistant foci was determined at 14 days after transfection and used to correct for any variability in transfection efficiency.

Transformation Assay

The NIH-3T3 cells were transfected with the various constructs and allowed to reach confluence after 48 hours as described above. Each 6 cm dish was split and seeded into 12 different 6 cm dishes. While 6 of them were made to grow in the presence of G-418 to detect transfection efficiency, the other six were grown in complete medium without G-418 and with a medium change every 4th day. The number of transformed foci were counted in these plates without G-418 and expressed as transformed foci per µg transfected DNA.

Anchorage-independent Cell Growth Assay

A limiting dilution technique (0.15 cell/well of a flat bottom 96-well-plate) was performed on transfectants grown in G-418 in order to isolate cell clones with different levels of HAAH activity as measured by Western blot analysis and enzymatic assay of hydroxylase activity. Cloned cell lines ($1.0 \times 10^4$ cells) were suspended in complete medium containing 0.4% low-melting agarose (SeaPlaque GTG Agarose; FMC Bioproducts, Rockland, Me.) and laid over a bottom agar mixture consisting of complete medium with 0.53% low-melting agarose. Each clone was assayed in triplicate. The clones were seeded under these conditions and 10 days later the size (positive growth >0.1 mm in diameter) and number of foci were determined.

Tumorigenicity in Nude Mice

The same clones as assessed in the anchorage independent growth assay were injected into nude mice and observed for tumor formation. Tumorigenicity was evaluated using 10 animals in each of 4 groups (Charles River Labs., Wilmington, Mass.). Group 1 received $1 \times 10^7$ cells stably transfected with mock DNA, Group 2–4 received $1 \times 10^7$ cells of clones stable transfected with pNH376 and expressing various levels of murine HAAH protein. Nude mice were kept under pathogen-free conditions in a standard animal facility. Thirty days after tumor cell inoculation, the animals were sacrificed using isofluorane (Aerrane, Anaquest, N.J.) containing chambers and the tumors were carefully removed and weight determined.

Animal Model of Bile Duct Proliferation

Following ligation of the common bile duct, intrahepatic bile duct proliferation was evident at 48 hours. Tissue samples obtained 8 and 16 days following common bile duct ligation revealed extensive bile duct proliferation as shown in Table 3.

TABLE 3

Bile duct proliferation and HAAH expression at different intervals after common bile duct ligation

| Group | Surgical Procedure | Microscopy* | Immunohisto-chemistry |
|---|---|---|---|
| 1 | no surgery | normal | negative |
| 2 | sham surgery | normal | negative |
| 3 | 6 hours post ligation | normal | negative |
| 4 | 12 hours post ligation | normal | negative |
| 5 | 24 hours post ligation | normal | negative |
| 6 | 48 hours post ligation | minimal bile duct prolif. | negative |
| 7 | 4 days post ligation | moderate bile duct prolif. | negative |
| 8 | 8 days post ligation | extensive bile duct prolif. | negative |
| 9 | 16 days post ligation | extensive bile duct prolif. | negative |

*Investigation was performed under light microscopy following a hematoxylin and eosin staining.

Immunohistochemical staining failed to detect presence of HAAH in proliferating bile ducts at any time. Analysis of HAAH expression in bile ducts derived from sham surgical controls was also negative, while all samples exhibited positive immunoreactivity with control antibodies to glyceraldehyde 3-phosphate dehydrogenase. Thus, bile duct proliferation was not associated with increased HAAH expression in this standard animal model system.

HAAH Expression in PSC

The liver biopsy specimens from patients with PSC exhibited bile duct proliferation accompanied by periductal fibrosis and a mononuclear inflammatory cell infiltrate without evidence of dysplasia. Adjacent sections immunostained with the an HAAH-specific monoclonal antibody had no detectable HAAH immunoreactivity in proliferating bile ducts. In contrast, sections of cholangiocarcinoma that were immunostained simultaneously using the same antibody and detection reagents manifested intense levels of HAAH immunoreactivity in nearly all tumor cells, whereas adjacent sections of the cholangiocarcinomas exhibited a negative immunostaining reaction with monoclonal antibody to Dengue virus. These findings indicate that HAAH expression was associated with malignant transformation rather than non-cancerous cellular proliferation of intrahepatic bile ducts.

HAAH Associated Transformation of NIH-3T3 Cells

The transforming capability of the murine and human AAH genes, as well as the murine AAH mutant construct without enzymatic activity were compared to mock DNA (negative control) and v-Src transfected NIH-3T3 cells (positive control). The transforming capability of murine AAH was found to be 2–3 times that of vector DNA control as shown in FIG. 1. The transforming capacity of the human gene was greater than that observed with the murine AAH ($32 \pm 1.5$ versus $13 \pm 2.6$ transformed foci, respectively). The murine and human AAH transfected cells formed large foci, resembling those of v-Src transfected fibroblasts, compared to the occasional much smaller foci observed in cells transfected with vector DNA that displayed the contact inhibition of fibroblast cell lines. Parallel experiments performed using the mutant pNH376-H660 construct without enzymatic activity revealed no transforming activity. This finding indicates that the enzymatic activity of HAAH is required for the transforming activity exhibited by the HAAH gene.

Anchorage-independent Cell Growth Assay

Figure 2:
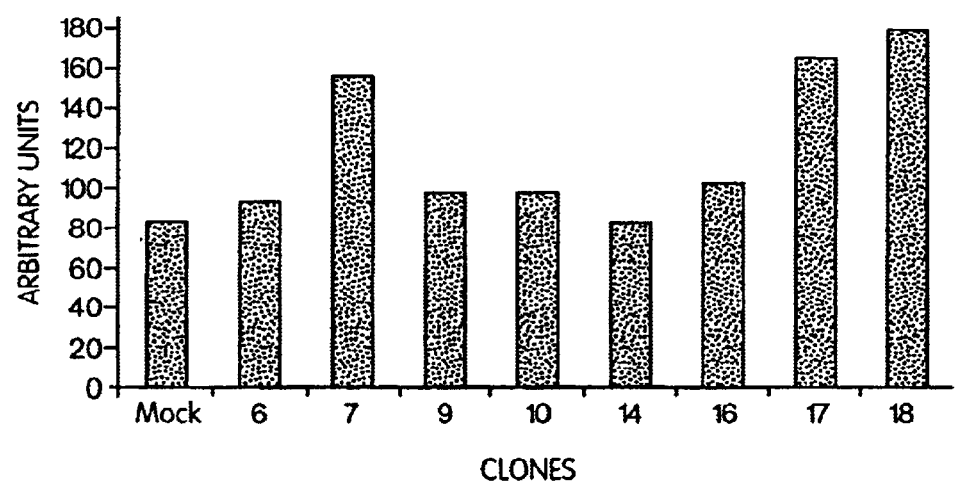
FIG. 2 is a bar graph showing the results of a densitometric analysis of a Western blot assay of proteins produced by various murine AAH stably transfected cell clones. In clones 7 and 18, there was a modest increase in HAAH gene expression, while the overexpression was to a lesser degree in clone 16.
Figure 3A:
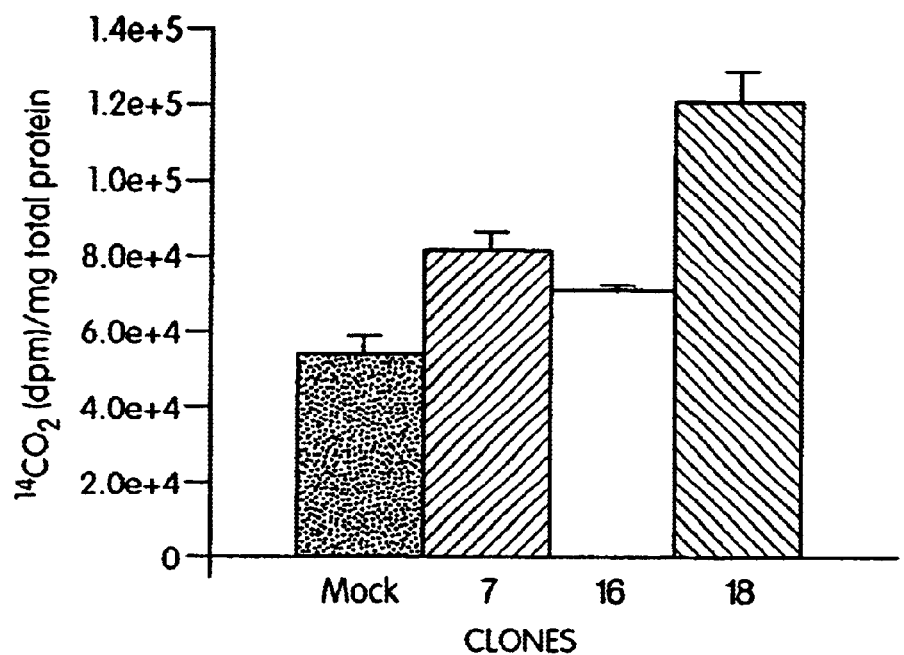
FIGS. 3A–B are bar graphs showing colony formation in soft agar exhibited by HAAH stably transfected clones compared to HAAH enzymatic activity.
Figure 3B:
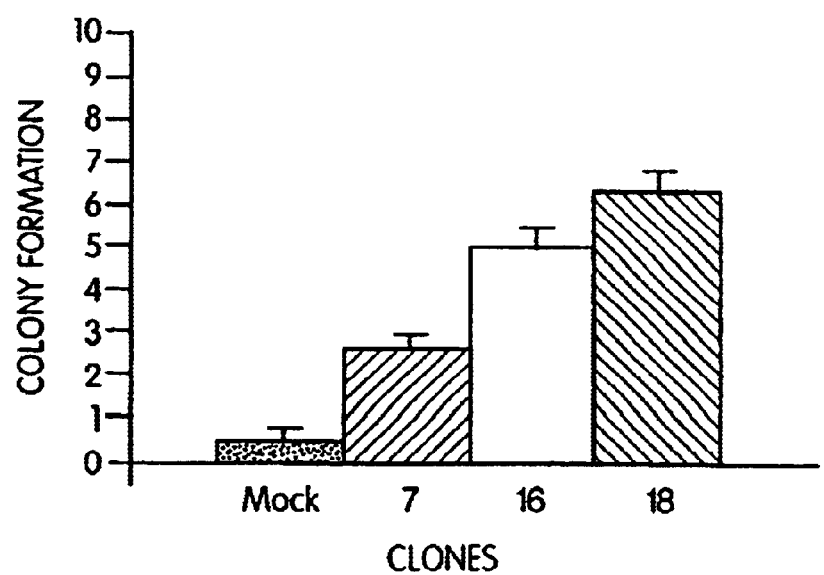

After transient transfection with the murine AAH construct, several different transformed foci were isolated for dilutional cloning experiments to establish stable transfected cell clones with different levels of HAAH gene expression. Nine different cloned cell lines were selected for further study. The expression level of the HAAH protein was determined by Western blot analysis. Clones 7 and 18 had a modest increase in HAAH protein expression, yet formed large colonies in soft agar (FIG. 2). Protein loading was equivalent in all lanes as shown by immunoblotting of the same membranes with an anti-Erk-1 monoclonal antibody. The increased protein expression was associated with increased enzymatic activity as shown in FIG. 3. The capability of these clones to exhibit anchorage independent cell growth in soft agar is presented in FIG. 3. All 3 clones with increased HAAH gene expression demonstrated anchorage independent cell growth compared to the mock DNA transfected clone.

Tumor Formation in Nude Mice

Figure 4:
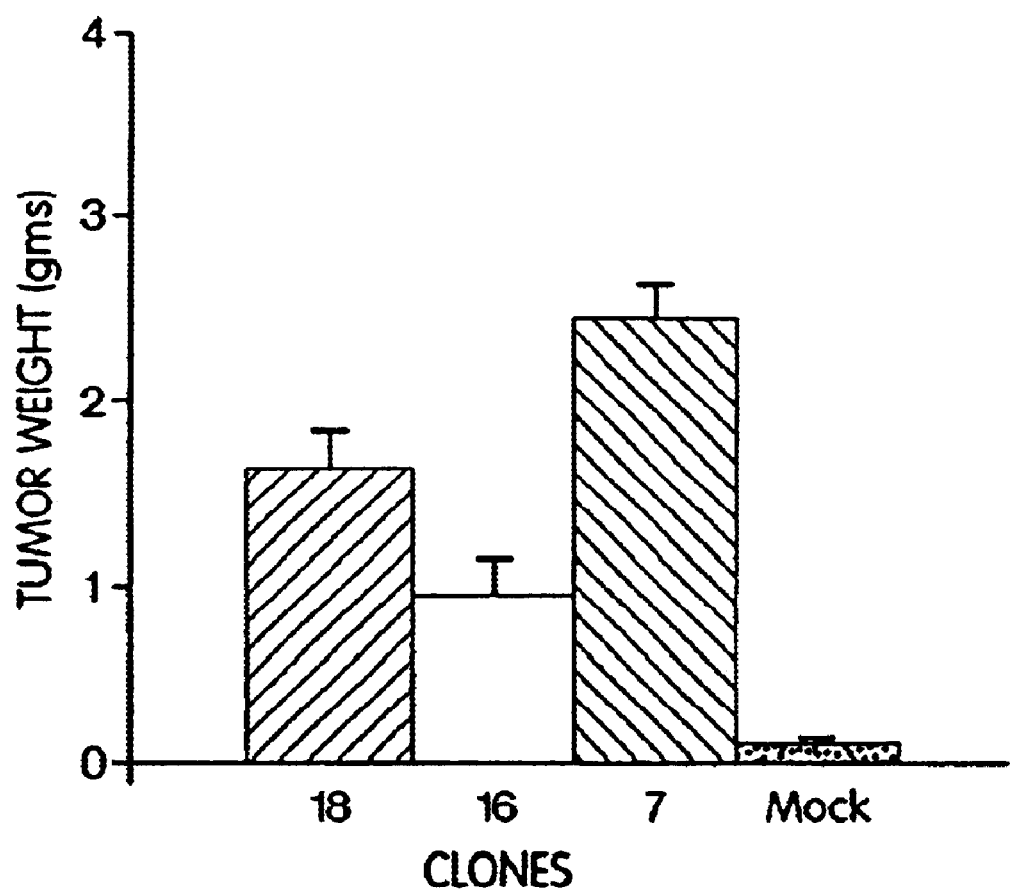
FIG. 4 is a bar graph showing tumor formation in nude mice injected with transfected clones overexpressing murine AAH. Tumor growth was assessed after 30 days. Mean tumor weight observed in mice injected with clones 7, 16 and 18 as compared to mock DNA transfected clone. All animals injected with clones overexpressing HAAH developed tumors.

The 3 clones with increased HAAH gene expression were evaluated for the ability to form tumors in nude mice. Tumor size in the mouse given clone 18 was compared to a mock DNA transfected clone. Clones 7, 16 and 18 were highly transformed in this assay and produced large tumors with a mean weight of 2.5, 0.9 and 1.5 grams, respectively (FIG. 4). These data indicate that overexpression of HAAH contributes to induction and maintenance of the malignant phenotype in vivo.

High Level HAAH Expression is Indicative of Malignancy

In order to determine if HAAH expression was associated with malignancy rather than increased cell turnover, two models of bile duct proliferation were studied. In the animal model, ligation of the common bile duct induced extensive intrahepatic bile duct proliferation, yet there was no evidence of HAAH gene expression under these experimental conditions as shown in Table 3. Similarly, HAAH gene expression was assessed in a human disease model associated with bile duct proliferation since PSC is an autoimmune liver disease associated with destruction as well as proliferation of the intra and extrahepatic bile ducts. PSC is premalignant disease, and a significant proportion of affected individuals will eventually develop cholangiocarcinoma. However, no evidence for increased HAAH gene expression in the presence of extensive bile duct proliferation.

Having established that HAAH protein levels were elevated in cholangiocarcinoma and not in normal or proliferating bile ducts, the role of HAAH in the generation of a malignant phenotype was studied. The HAAH gene was transfected into NIH-3T3 cells and cellular changes, e.g., increased formation of transformed foci, colony growth in soft agar and tumor formation in nude mice associated with malignant transformation, were evaluated. The full-length murine and human AAH genes were cloned into expression constructs and transiently transfected into NIH-3T3 cells. An increased number of transformed foci was detected in cells transfected both with the murine and human AAH genes as compared to mock DNA transfected controls. The increased number of transformed foci, after controlling for transfection efficiency, was not as high compared to v-Src gene transfected cells used as a positive control. The enzymatic activity of the HAAH gene was required for a malignant phenotype because a mutant construct which abolished the catalytic site had no transforming properties. Several stable transfectants and cloned NIH-3T3 cell lines with a modest increase in HAAH protein levels and enzymatic activity were established. Such cell lines were placed in soft agar to examine anchorage independent cell growth as another property of the malignant phenotype. All cell lines grew in soft agar compared to mock DNA transfected control, and there was a positive correlation between the cellular level of HAAH gene expression and the number and size of colonies formed. Three of these cloned cell lines formed tumors in nude mice. All three cell lines with increased HAAH expression were oncogenic as shown by the development of large tumors as another well-known characteristic of the transformed phenotype.

To determine whether cellular changes induced by overexpression of HAAH were related to the enzymatic function, a site-directed mutation was introduced into the gene that changed the ferrous iron binding site from histidine to lysine at 660th position of mouse HAAH thereby abolishing hydroxylase activity of the murine HAAH. A corresponding mutation in HAAH is used as a dominant negative mutant to inhibit HAAH hydroxylase activity. The pNH376-H660 construct had no transformation activity indicating cellular changes of the malignant phenotype induced by overexpression depends on the enzymatic activity of the protein.

Notch receptors and their ligands have several EGF-like domains in the N-terminal region that contain the putative consensus sequence for beta-hydroxylation. Notch ligands are important elements of the Notch signal transduction pathway and interaction of Notch with its ligands occurs by means of EGF-like domains of both molecules. Point mutations affecting aspartic acid or asparagine residues in EGF-like domains that are the targets for beta-hydroxylation by HAAH reduce calcium binding and protein-protein interactions involved in the activation of downstream signal transduction pathways. Overexpression of HAAH and Notch protein hydroxylation by HAAH contributes to malignancy. Tumor growth is inhibited by decreasing Notch protein hydroxylation by HAAH The data presented herein is evidence that high-level HAAH expression is linked to malignant transformation. An increase in expression of the HAAH cDNA in NIH-3T3 cells induced a transformed phenotype manifested by increased numbers of transformed foci, anchorage-independent growth, and tumorigenesis in nude mice. In addition, intact HAAH-enzyme was found to be required for HAAH-associated transformation. Accordingly, inhibition of as little as 20% of endogenous HAAH enzymatic activity or expression confers a therapeutic benefit. For example, clinical benefit is achieved by 50%–70% inhibtion of HAAH expression or activity after administaration of an HAAH inhibitory compound compared to the level associated with untreated cancer cell or a normal noncancerous cell.

HAAH is regulated at the level of transcription. Only modest increases in HAAH expression and enzyme activity were required for cellular transformation. These results indicate that increased HAAH gene expression and enzyme activity contribute to the generation or maintenance of the transformed phenotype and that decreasing transcription of the HAAH gene or decreasing enzymatic activity of the HAAH gene product leads to a decrease in malignancy. Accordingly, HAAH transcription is inhibited by administering compounds which decrease binding of Fos and/or Jun (elements which regulate HAAH transcription) to HAAH promoter sequences.

Since HAAH is up-regulated with malignant transformation of bile duct epithelium, and HAAH immunoreactivity is detectable on tumor cell surface membranes, HAAH is also a molecule to which to target a cytotoxic agent, e.g., by linking the cytotoxic agent to a compound that binds to HAAH expressed on the surface of a tumor cell. Assay of HAAH protein levels in either biological fluids such as bile, or cells obtained by fine needle aspiration is a diagnostic marker of human cholangiocarcinoma.

EXAMPLE 2

Expression of AAH and Growth and Invasiveness of Malignant CNS Neoplasms

AAH is abundantly expressed in carcinomas and trophoblastic cells, but not in most normal cells, including those of CNS origin. High levels of AAH expression were observed in 15 of 16 glioblastomas, 8 of 9 anaplastic oligodendrogliomas, and 12 of 12 primitive neuroectodermal tumors (PNETs). High levels of AAH immunoreactivity were primarily localized at the infiltrating edges rather than in the central portions of tumors. Double-label immunohistochemical staining demonstrated a reciprocal relationship between AAH and tenascin, a substrate for AAH enzyme activity. PNET2 neuronal cell lines treated with phorbol ester myristate or retinoic acid to stimulate neuritic extension and invasive growth exhibited high levels of AAH expression, whereas $H_2O_2$-induced neurite retraction resulted in down-regulation of AAH. PNET2 neuronal cells that stably over-expressed the human AAH cDNA had increased levels of PCNA and Bcl-2, and reduced levels of p21/Waf1 and p16, suggesting that AAH overexpression results in enhanced pathological cell proliferation, cell cycle progression, and resistance to apoptosis. In addition, the reduced levels of p16 observed in AAH-transfectants indicate that AAH over-expression confers enhanced invasive growth of neoplastic cells since deletion or down-regulation of the p16 gene correlates with more aggressive and invasive in vivo growth of glioblastomas. Increased AAH immunoreactivity was detected at the infiltrating margins of primary malignant CNS neoplasms, further indicating a role of HAAH in tumor invasiveness.

The following materials and methods were used to generate the data described below.

Analysis of AAH Immunoreactivity in Primary Human Malignant CNS Neoplasms

AAH immunoreactivity was examined in surgical resection specimens of glioblastoma (N=16), anaplastic oligodendroglioma (N=9), and primitive neuroectodermal tumor (PNET; supratentorial neuroblastomas (N=3) and medulloblastomas (N=9). The histopathological sections were reviewed to confirm the diagnoses using standard criteria. Paraffin sections from blocks that contained representative samples of viable solid tumor, or tumor with adjacent intact tissue were studied. Sections from normal adult postmortem brains (N=4) were included as negative controls. AAH immunoreactivity was detected using qn HAAH-specific monoclonal antibody. Immunoreactivity was revealed by the avidin-biotin horseradish peroxidase complex method (Vector ABC Elite Kit; Vector Laboratories, Burlingame, Calif.) using 3-3' diaminobenzidine (DAB) as the chromogen (24) and hematoxylin as a counterstain.

Tenascin and laminin are likely substrates for AAH due to the presence of EGF-like repeats within the molecules. Double-immunostaining studies were performed to co-localize AAH with tenascin or laminin. The AAH immunoreactivity was detected by the ABC method with DAB as the chromogen, and tenascin or laminin immunoreactivity was detected by the avidin-biotin alkaline phosphatase complex method (Vector Laboratories, Burlingame, Calif.) with BCIP/NBT as the substrate. As positive and negative controls, adjacent sections were immunostained with monoclonal antibody to glial fibrillary acidic protein (GFAP) and Hepatitis B surface antigen. All specimens were batch immunostained using the same antibody dilutions and immunodetection reagents.

Cell Lines and Culture Conditions

Studies were conducted to determine whether AAH expression was modulated with neurite (filopodia) extension (sprouting) as occurs with invasive growth of malignant neoplasms. Human PNET2 CNS-derived and SH-Sy5y neuroblastoma cells were cultured and stimulated for 0, 1, 2, 3, 5, or 7 days with 100 nM phorbol 12-ester 13-acetate or 10 $\mu$M retinoic acid to induce sprouting. In addition, to examine the effects of neurite retraction on AAH expression, subconfluent cultures were treated for 24 hours with low concentrations (10–40 $\mu$M) of $H_2O_2$. For both studies, AAH expression was evaluated by Western blot analysis using the an HAAH-specific antibody.

Generation of PNET2 AAH-transfected Clones

The full-length human AAH cDNA (SEQ ID NO:3) was ligated into the pcDNA3.1 mammalian expression vector in which gene expression was under the control of a CMV promoter (Invitrogen Corp., San Diego, Calif.). PNET2 cells were transfected with either pHAAH or pcDNA3 (negative control) using Cellfectin reagent (Gibco BRL, Grand Island, N.Y.). Neomycin-resistant clones were selected for study if the constitutive levels of AAH protein expression were increased by at least two-fold relative to control (pcDNA3) as detected by Western blot analysis. To determine how AAH overexpression altered the expression of genes that modulate the transformed phenotype, the levels of proliferating cell nuclear antigen (PCNA), p53, p21/Waf1, Bcl-2, and p16 were measured in cell lysates prepared from subconfluent cultures of AAH (N=5) and pcDNA3 (N=5) stably transfected clones. PCNA was used as marker of cell proliferation. p53, p21/Waf1, and Bcl-2 levels were examined to determine whether cells that over-expressed AAH were more prone to cell cycle progression and more resistant to apoptosis. The levels of p16 were assessed to determine whether AAH over-expression has a role in tumor invasiveness.

Western Blot Analysis

Cells grown in 10 $cm^2$ dishes were lysed and homogenized in a standard radioimmunoprecipitation assay RIPA buffer containing protease and phosphatase inhibitors. The supernatants collected after centrifuging the samples at 12,000×g for 10 minutes to remove insoluble debris were used for Western blot analysis. Protein concentration was measured using the BCA assay (Pierce Chemical Co, Rockford, Ill.). Samples containing 60 $\mu$g of protein were electrophoresed in sodium dodecyl sulfate polyacrylamide gels (SDS-PAGE) and subjected to Western blot analysis. Replicate blots were probed with the individual antibodies. Immunoreactivity was detected with horseradish peroxidase conjugated IgG (Pierce Chemical Co, Rockford, Ill.) and enhanced chemiluminescence reagents. To quantify the levels of protein expression, non-saturated autoradiographs were subjected to volume densitometry using NIH Image software, version 1.6. Statistical comparisons between pHAAH and pcDNA3 transfected cells were made using Student T tests.

Antibodies

HAAH-specific monoclonal antibody generated against the FOCUS hepatocellular carcinoma cells were used to detect AAH immunoreactivity. Monoclonal antibodies to tenascin, and glial fibrillary acidic protein, and rabbit polyclonal antibody to laminin were purchased from Sigma Co (St. Louis, Mo.). Rabbit polyclonal antibody to human p16 was purchased from Santa Cruz Biotechnology Inc. (Santa Cruz, Calif.). The 5C3 negative control monoclonal antibody to Hepatitis B surface antigen was generated using recombinant protein and used as a negative control.

AAH Immunoreactivity in Primary Malignant Brains Tumors

AAH immunoreactivity was detected in 15 of 16 glioblastomas, 8 of 9 anaplastic oligodendrogliomas, and all 12 PNETs. AAH immunoreactivity was localized in the cytoplasm, nucleus, and cell processes. The tissue distribution of AAH immunoreactivity was notable for the intense labeling localized at the interfaces between tumor and intact brain, and the conspicuously lower levels of immunoreactivity within the central portions of the tumors. High levels of AAH immunoreactivity were also observed in neoplastic cells distributed in the subpial zones, leptomeninges, Virchow-Robin perivascular spaces, and in individual or small clusters of neoplastic cells that infiltrated the parenchyma. In contrast, AAH immunoreactivity was not detectable in normal brain. The distribution of AAH immunoreactivity appeared not to be strictly correlated with DNA synthesis since the density of nuclei in mitosis (1–5%) was similar in the central and peripheral portions of the tumors.

Relationship between AAH and Tenascin Immunoreactivity in Glioblastomas

Tenascin is an extracellular matrix-associated antigen expressed in malignant gliomas. Tenascin contains EGF-like domains within the molecule, a substrate for HAAH hydroxylation. To localize AAH in relation to tenascin immunoreactivity in malignant brain tumors, double-label immunohistochemical staining was performed in which AAH was detected using a brown chromogen (DAB), and tenascin, a blue chromogen (BCIP/NBT). Adjacent sections were similarly double-labeled to co-localize AAH with laminin, another EGF domain containing extracellular matrix molecule expressed in the CNS. Intense levels of tenascin immunoreactivity were observed in perivascular connective tissue and in association with glomeruloid proliferation of endothelial cells. The double-labeling studies demonstrated a reciprocal relationship between AAH and tenascin immunoreactivity such that high levels of AAH were associated with low or undetectable tenascin, and low levels of AAH were associated with abundant tenascin immunoreactivity. Although laminins are also likely substrates for AAH enzyme activity due to the EGF repeats within the molecules, double labeling studies revealed only low levels of laminin immunoreactivity throughout the tumors and at interfaces between tumor and intact tissue.

Analysis of AAH Expression in Neuronal Cell Lines Treated with PMA or RA

Figure 5A:
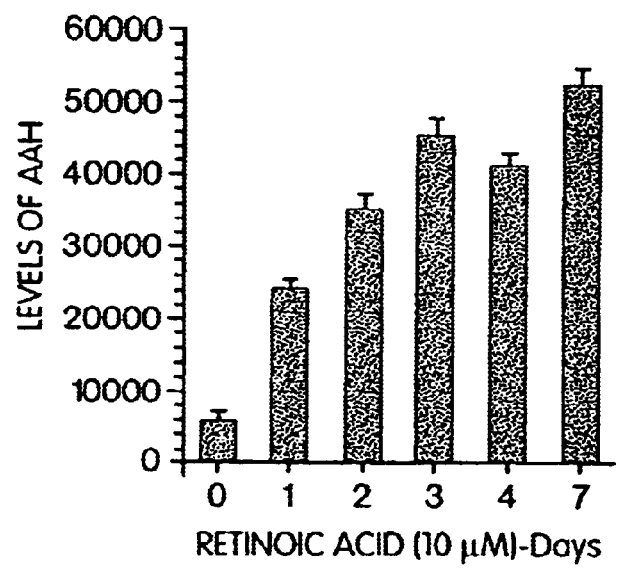
FIGS. 5A–D are bar graphs showing increased AAH expression in PNET2 (FIGS. 5A, 5C) and SH-Sy5y (FIG. 5B) cells treated with retinoic acid (FIGS. 5A, 5B) or phorbol ester myristate (PMA.
Figure 5B:
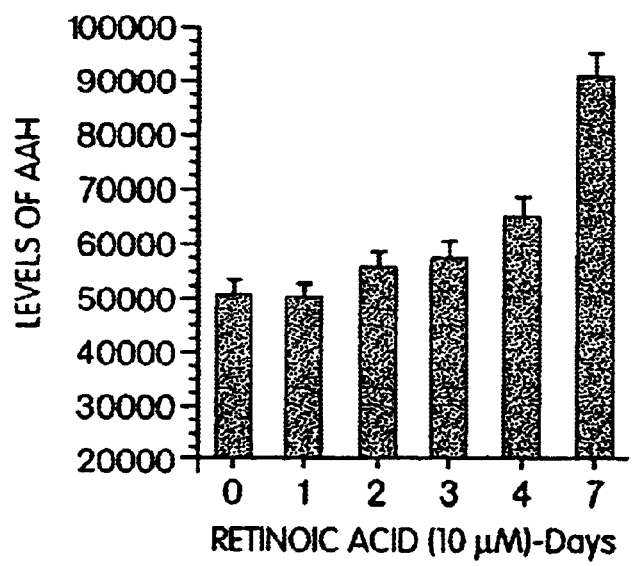
Figure 5C:
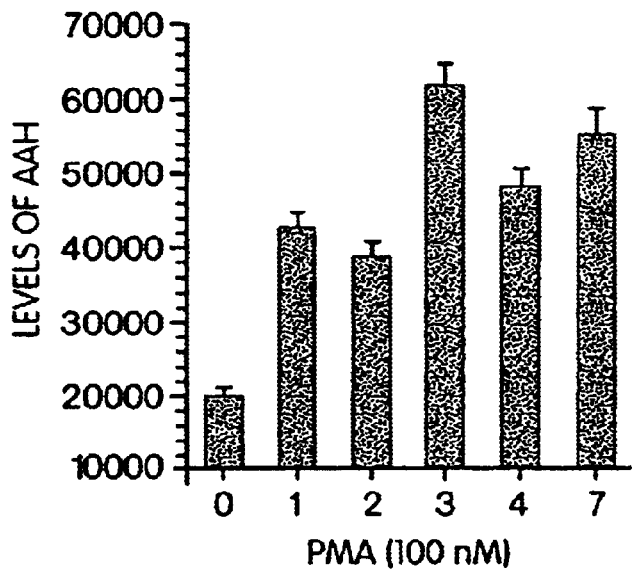

Neuritic sprouting/filopodia extension marks invasive growth of neoplastic neuronal cells. PMA activates protein kinase C signal transduction pathways that are involved in neuritic sprouting. Retinoic acid binds to its own receptor and the ligand-receptor complex translocates to the nucleus where it binds to specific consensus sequences present in the promoter/enhancer regions of target genes involved in neuritic growth. Both PNET2 and SH-Sy5y cells can be induced to sprout by treatment with PMA (60–120 nM) or retinoic acid (5–10 $\mu$M). FIGS. 5A–D depict data from representative Western blot autoradiographs; the bar graphs correspond to the mean ±S.D. of results obtained from three experiments. Western blot analysis with the FB50 antibody detected doublet bands corresponding to protein with an molecular mass of approximately 85 kDa. Untreated PNET2 cells had relatively low levels of AAH immunoreactivity (FIG. 5A), whereas untreated SH-Sy5y cells had readily detected AAH expression (FIG. 5B). Untreated PNET2 cells exhibited polygonal morphology with coarse, short radial cell processes, whereas SH-Sy5y cells were slightly elongated and spontaneously extend fine tapered processes. Both cell lines manifested time-dependent increases in the levels of AAH immunoreactivity following either RA (FIGS. 5A and 5B) or PMA (FIG. 5C) stimulation and neurite extension. In PNET2 cells, the levels of AAH protein increased by at least two-fold 24 hours after exposure to RA or PMA, and high levels of AAH were sustained throughout the 7 days of study. In SH-Sy5y cells, the RA- or PMA-stimulated increases in AAH expression occurred more gradually and were highest after 7 days of treatment (FIG. 5B).

Figure 5D:
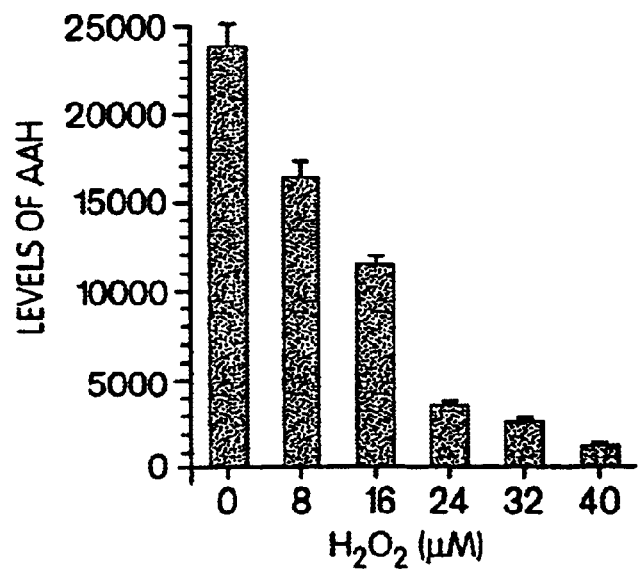

To examine the effect of AAH expression on neurite retraction, PNET2 and SH-Sy5y cells were treated with low concentrations (8–40 $\mu$M) of $H_2O_2$. After 24 hours exposure to up to 40 $\mu$M $H_2O_2$, although most cells remained viable (Trypan blue dye exclusion), they exhibited neurite retraction and rounding. Western blot analysis using the FB50 antibody demonstrated H202 dose-dependent reductions in the levels of AAH protein (FIG. 5D).

Effects of AAH Over-expression in PNET2 Cells

To directly assess the role of AAH overexpression in relation to the malignant phenotype, PNET2 cells were stably transfected with the human full-length cDNA with gene expression under control of a CMV promoter (pHAAH). Neomycin-resistant clones that had at least two-fold higher levels of AAH immunoreactivity relative to neomycin-resistant pcDNA3 (mock) clones were studied. Since aggressive behavior of malignant neoplasms is associated with increased DNA synthesis, cell cycle progression, resistance to apoptosis, and invasive growth, the changes in phenotype associated with constitutive over-expression of AAH were characterized in relation to PCNA, p21/Waf1, p53, Bcl-2, and p16. PCNA was used as an index of DNA synthesis and cell proliferation. p21/Waf1 is a cell cycle inhibitor. Expression of the p53 tumor-suppressor gene increases prior to apoptosis, whereas bcl-2 inhibits apoptosis and enhances survival of neuronal cells. p16 is an oncosuppressor gene that is often either down-regulated or mutated in infiltrating malignant neoplasms.

Figure 6:
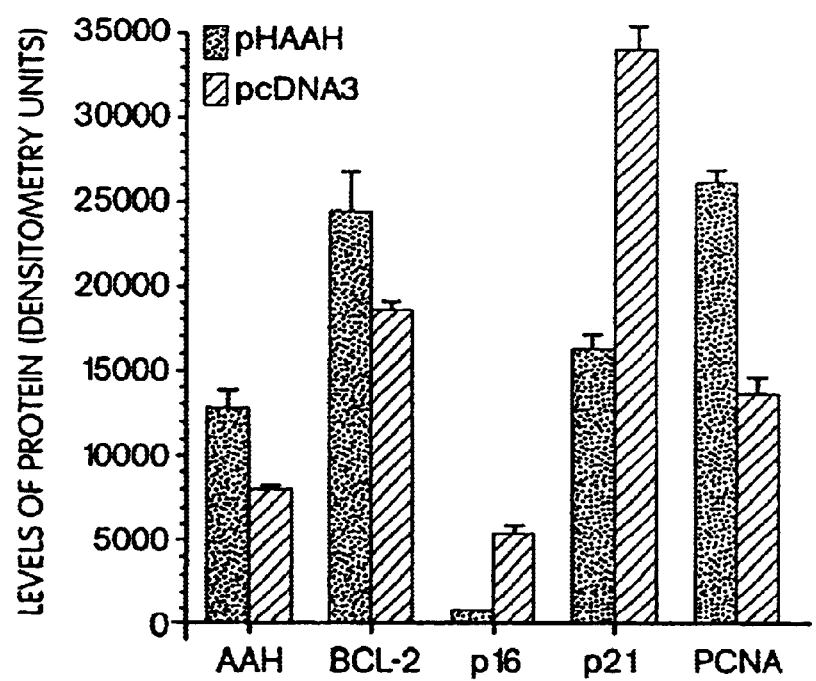
FIG. 6 is a bar graph showing the effects of AAH over-expression on the levels of anti-apoptosis (Bcl-2), cell cycle-mitotic inhibitor (p16 and p21/Waf1), and proliferation (proliferating cell nuclear antigen; PCNA) molecules. PNET2 neuronal cells were stably transfected with the full-length human cDNA encoding AAH (pHAAH) or empty vector (pcDNA). AAH gene expression was under control of a CMV promoter. Western blot analysis was performed with cell lysates prepared from cultures that were 70 to 80 percent confluent. Protein loading was equivalent in each lane. Replicate blots were probed with the different antibodies. Bar graphs depict the mean S.D.'s of protein expression levels measured in three experiments. All differences are statistically significant by Student T-test analysis ($P<0.01$–$P<0.001$).
Figure 7:
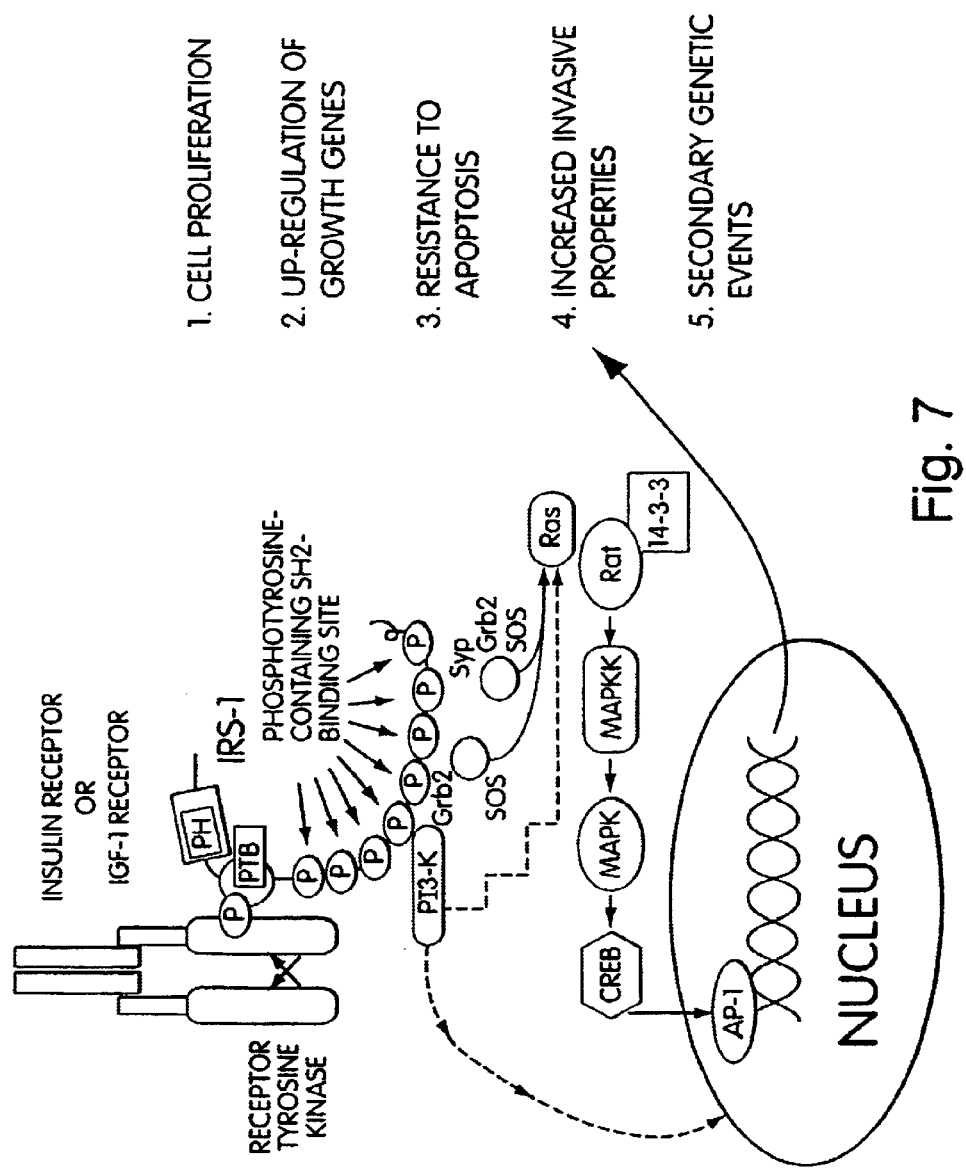
FIG. 7 is a diagram of showing the components of the IRS-1 signal transduction pathway.

Five pHAAH and 5 pcDNA3 clones were studied. Increased levels of AAH expression in the pHAAH transfected clones was confirmed by Western (FIG. 6) and Northern blot analyses. Western blot analysis using cell lysates from cultures that were 70 to 80 percent confluent demonstrated that constitutively increased levels of AAH expression (approximately 85 kDa; $P<0.05$) in pHAAH-transfected cells were associated with significantly increased levels of PCNA (approximately 35 kDa; $P<0.01$) and Bcl-2 (approximately 25 kDa; $P<0.05$), and reduced levels of p21/Waf1 (approximately 21 kDa; $P<0.001$) and p16 (approximately 16 kDa; $P<0.001$) (FIG. 6). However, the pHAAH stable transfectants also exhibited higher levels of wild-type p53 (approximately 53–55 kDa). Although AAH expression (85 kDa protein) in the stable transfectants was increased by only 75 to 100 percent, the levels of p16 and p21/Waf1 were sharply reduced, and PCNA increased by nearly two-fold (FIG. 6).

Increased AAH Expression is Indicative of Growth and Invasiveness of Malignant CNS Neoplasms The data described herein demonstrates that AAH overexpression is a diagnostic tool by which to identify primary malignant CNS neoplasms of both neuronal and glial cell origin. Immunohistochemical staining studies demonstrated that AAH overexpression was detectable mainly at the interfaces between solid tumor and normal tissue, and in infiltrating neoplastic cells distributed in the subpial zones, leptomeninges, perivascular spaces, and parenchyma. In vitro experiments demonstrated that AAH gene expression was modulated with neurite (filopodium) extension and invasiveness and down-regulated with neurite retraction. In addition, PNET2 cells stably transfected with the AAH cDNA exhibited increased PCNA and bcl-2, and reduced Waf1/p21 and p16 expression. Therefore, AAH overexpression contributes to the transformed phenotype of CNS cells by modulating the expression of other genes that promote cellular proliferation and cell cycle progression, inhibit apoptosis, or enhance tumor cell invasiveness.

The data demonstrated readily detectable AAH mRNA transcripts (4.3 kB and 2.6 kB) and proteins (85 kDa and 50–56 kDa) in PNET2 and SH-Sy5y cells, but not in normal brain. Correspondingly, high levels of AAH immunoreactivity were observed in 35 of the 37 in malignant primary CNS-derived neoplasms studied, whereas the 4 normal control brains had no detectable AAH immunoreactivity. The presence of high-level AAH immunoreactivity at the infiltrating margins and generally not in the central portions of the tumors indicates that AAH overexpression is involved in the invasive growth of CNS neoplasms. Administration of compounds which decrease AAH expression or enzymatic activity inhibits proliferation of CNS tumors which overexpress AAH, as well as metastases of CNS tumors to other tissue types.

The AAH enzyme hydroxylates EGF domains of a number of proteins. Tenascin, an extracellular matrix molecule that is abundantly expressed in malignant gliomas, contains EGF-like domains. Since tenascin promotes tumor cell invasion, its abundant expression in glioblastomas represents an autocrine mechanism of enhanced tumor cell growth vis-α-vis the frequent overexpression of EGF or EGF-like receptors in malignant glial cell neoplasms. Analysis of the functional domains of tenascins indicated that the mitogenic effects of this family of molecules are largely mediated by the fibronectin domains, and that the EGF-like domains inhibit growth, cell process elongation, and matrix invasion. Therefore, hydroxylation of the EGF-like domains by AAH represents an important regulatory factor in tumor cell invasiveness.

Double-label immunohistochemical staining studies demonstrated a reciprocal relationship between AAH and tenascin immunoreactivity such that high levels AAH immunoreactivity present at the margins of tumors were associated with low levels of tenascin, and low levels of AAH were often associated with high levels of tenascin. These observations indicated that AAH hydroxylation of EGF-like domains of tenascin alters the immunoreactivity of tenascin protein, and in so doing, facilitates the invasive growth of malignant CNS neoplasms into adjacent normal tissue and perivascular spaces.

AAH immunoreactivity was examined in PNET2 and SH-Sy5y neuronal cells induced to undergo neurite extension with PMA or retinoic acid, or neurite retraction by exposure to low doses of $H_2O_2$. AAH expression was sharply increased by PMA- or retinoic acid-induced neurite (filopodium) extension, and inhibited by H2O2-induced neurite retraction and cell rounding. Neurite or filopodium extension and attachment to extracellular matrix are required for tumor cell invasion in the CNS. The EGF-like domains of tenascin inhibit neuritic and glial cell growth into the matrix during development.

To directly examine the role of AAH overexpression in relation to the transformed phenotype, genes modulated with DNA synthesis, cell cycle progression, apoptosis, and tumor invasiveness were examined in neuronal cell clones that stably over-expressed the human AAH cDNA. The findings of increased PCNA and reduced Waf1/p21 immunoreactivity indicated that AAH overexpression enhances cellular proliferation and cell cycle progression. In addition, the finding of increased Bcl-2 expression indicated that AAH overexpression contributes to the transformed phenotype by increasing cellular resistance to apoptosis. The apparently contradictory finding of higher levels of p53 in the cells that overexpressed AAH is explained by the observation that high levels of wildtype p53 in immature neuronal cells were associated with neuritic growth (invasiveness) rather than apoptosis. Levels of p16 were reduced (compared to normal cells) or virtually undetectable in cells that constitutively overexpressed AAH; a deletion mutation of the p16 gene has been correlated with invasive growth and more rapid progression of malignant neoplasms, including those of CNS origin. These data indicate that p16 expression is modulated by AAH.

EXAMPLE 3
Increased HAAH Production and IRS-mediated Signal Transduction

IRS-1 mediated signal transduction pathway is activated in 95% of human HCC tumors compared to the adjacent uninvolved liver tissue. HAAH is a downstream effector gene involved in this signal transduction pathway. HAAH gene upregulation is closely associated with overexpression of IRS-1 in HCC tumors as revealed by immunohistochemical staining and Western blot analysis. A high level of HAAH protein is expressed in HCC and cholangiocarcinoma compared to normal hepatocytes and bile ducts. Both of these tumors also exhibit high level expression of IRS-1 by immunohistochemical staining. FOCUS HCC cell clones stably transfected with a C-terminal truncated dominant negative mutant of IRS-1, which blocks insulin and IGF-1 stimulated signal transduction, was associated with a striking reduction in HAAH gene expression in liver. In contrast, transgenic mice overexpressing IRS-1 demonstrate an increase in HAAH gene expression by Western blot analysis. Insulin stimulation of FOCUS HCC cells (20 and 40 U) in serum free medium and after 16 hr of serum starvation demonstrated upregulation of HAAH gene expression. These data indicate that HAAH gene expression is a downstream effector of the IRS-1 signal transduction pathway.

EXAMPLE 4
Effects of HAAH Expression Levels on the Characteristics of the Malignant Phenotype Overexpression of IRS-1 in NIH 3T3 cells induces transformation. The full-length murine HAAH construct was cloned into the pcDNA3 eukaryotic expression vector. A second murine construct encoded HAAH with abolished catalytic activity due-to a site directed mutation. The full-length human HAAH cDNA was cloned into the pcDNA3 expression vector as well as a plasmid that encodes v-src which was used as a positive control for transformation activity. Standard methods were used for transfection of NIH 3T3 cells, control for transfection efficiency, assays of HAAH enzymatic activity, transformation by analysis of foci formation, anchorage-independent cell growth assays and analysis of tumorigenicity in nude mice. The data indicate that HAAH overexpression is associated with generation of a malignant phenotype.

TABLE 4

Overexpression of enzymatically active HAAH indicates malignancy

| cDNA | # of foci ± S.D.[b] | NIH 3T3 clone | # of colonies[e] |
|---|---|---|---|
| pcDNA3 (mock) | 6.0 ± 3.3 | pcDNA (mock) | 0.4 ± 0.5 |
| murine AAH | 14.0 ± 2.9 | clone 18[d] | 6.2 ± 2.9 |
| mutant murine AAH[a] | 1.6 ± 1.0 | clone 16[e] | 4.7 ± 6.5 |
| human AAH | 32.0 ± 5.4 | | |
| v-scr | 98.0 ± 7.1 | | |

[a] enzymatically inactive AAH
[b] $P < 0.01$ compared to mock and mutant murine AAH
[c] $P < 0.001$ compared to mock
[d] Clone 18 is a stable cloned NIH 3T3 cell line that overexpression human HAAH by approximately two fold.
[e] Clone 16 is a stable cloned NIH 3T3 cell line that overexpresses human HAAH by about 50%.

These data indicate that overexpression of HAAH is associated with formation of transformed foci. Enzymatic activity is required for cellular transformation to occur. Cloned NIH 3T3 cell lines with increased human HAAH gene expression grew as solid tumors in nude mice. HAAH is a downstream effector gene of the IRS-1 signal transduction pathway.

EXAMPLE 5
Inhibition of HAAH Gene Expression

The FOCUS HCC cell line from which the human HAAH gene was initially cloned has a level of HAAH expression that is approximately 3–4 fold higher than that found in normal liver. To make an HAAH antisense construct, the full length human HAAH cDNA was inserted in the opposite orientation into a retroviral vector containing a G418 resistant gene, and antisense RNA was produced in the cells. Shorter HAAH antisense nucleic acids, e.g., those corresponding to exon 1 of the HAAH gene are also used to inhibit HAAH expression.

Figure 8:
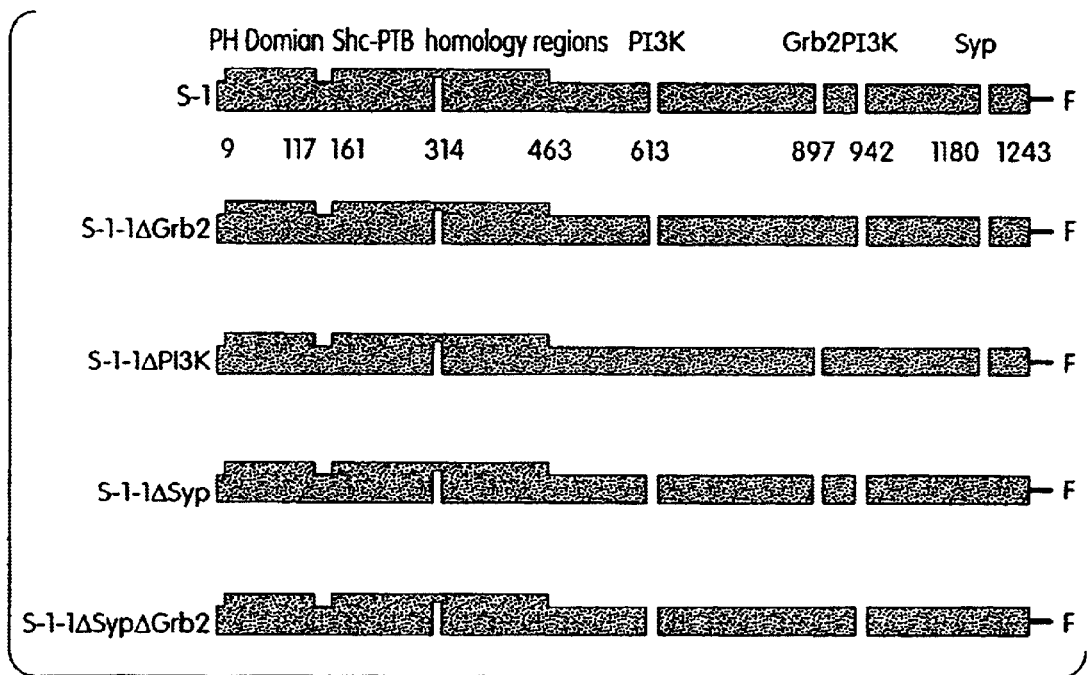
FIG. 8 is a line graph showing growth curves generated in cells expressing the antisense HAAH compared to controls expressing GFP.
Figure 9:
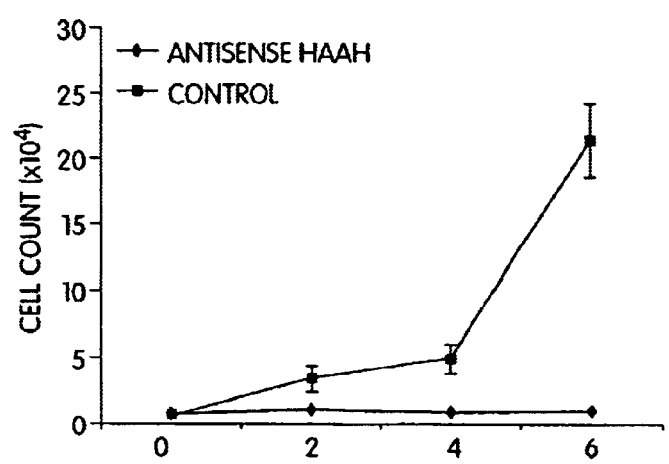
FIG. 9 is a diagram of the functional domains of the hIRS-1 protein and structural organization of the point mutants. All mutant and "wild type" hIRS-1 proteins construct contain a FLAG (F) epitope (DYKDDDDK; SEQ ID NO:7) at the C-terminus. PH and PTB indicate pleckstrin homology and phosphotyrosine binding, regions, respectively.

FOCUS cells were infected with this vector and the level of HAAH was determined by Western blot analysis. A reduction in HAAH gene expression was observed. Growth rate and morphologic appearance of cells infected with a retrovirus containing a nonrelevant Green Fluorescent Protein (GFP) also inserted in the opposite orientation as a control (FIG. 8). Cells (harboring the HAAH antisense construct) exhibited a substantial change in morphology characterized by an increase in the cytoplasm to nuclear ratio as well as assuming cell shape changes that were reminiscent of normal adult hepatocytes in culture. Cells with reduced HAAH levels grew at a substantially slower rate than retroviral infected cells expressing antisense (GFP) (control) as shown in FIG. 8. A reduction in HAAH gene expression was associated with a more differentiated non-cancerous "hepatocyte like" phenotype. Expression of HAAH antisense sequences are used to inhibit tumor growth rate. Reduction of HAAH cellular levels results in a phenotype characterized by reduced formation of transformed foci, low level or absent anchorage independent growth in soft agar, morphologic features of differentiated hepatocytes as determined by light and phase contrast microscopy, and no tumor formation (as tested by inoculating the cells into nude mice).

EXAMPLE 6
Human IRS-1 Mutants

Insulin/IGF-1 stimulated expression of HAAH in HCC cell lines. Dominant-negative IRS-1 cDNAs mutated in the plextrin and phosphotryosine (PTB) domains, and Grb2, Syp and PI3K binding motifs located in the C-terminus of the molecule were constructed. Human IRS-1 mutant constructs were generated to evaluate how HAAH gene expression is upregulated by activation of the IRS-1 growth factor signal transduction cascade. Specific mutations in the C terminus of the hIRS-1 molecule abolished the various domains which bind to SH2-effector proteins such as Grb2, Syp and PI3K. The human IRS-1 protein contains the same Grb2 and Syp binding motifs of 897YVNI (underlined in Table 5, below and 1180YIDL (underlined in Table 5, below), respectively, as the rat IRS-1 protein. Mutants of hIRS-1 were constructed by substitution of a TAT codon (tyrosine) with a TTT codon (phenylalanine), in these motifs by use of oligonucleotide-directed mutagenesis suing the following primers: (5'-GGGGGAATTTGTCAATA-3' (SEQ ID NO:8) and 5'-GAATTTGTTAATATTG-3' (SEQ ID NO:9), respectively). The cDNAs of hIRS-1 (wild-type) and mutants (tyrosine 897-to-phenylalanine and tyrosine 1180-to-phenylalanine) were subcloned into the pBK-CMV expression vector and designated as hIRS-1-wt, 897F, Δ-Grb2), 1180F, and ΔSyp.

TABLE 5

Human IRS-1 amino acid sequence

| | | | | | | |
|---|---|---|---|---|---|---|
| MASPPESDGF | SDVRKVGYLR | KPKSMHKRFF | VLRAASEAGG | PARLEYYENE | KKWRHKSSAP | 61 |
| KRSIPLESCF | NINKRADSKN | KHLVALYTRD | EHFAIAADSE | AEQDSWYQAL | LQLHNRAKGH | 121 |
| HDGAAALGAG | GGGGSCSGSS | GLGEAGEDLS | YGDVPPGPAF | KEVWQVILKP | KGLGQTKNLI | 181 |
| GIYRLCLTSK | TISFVKLNSE | AAAVVLQLMN | IRRCGHSENF | FFIEVGRSAV | TGPGEFWMQV | 241 |
| DDSVVAQNMH | ETILEAMRAM | SDEFRPRSKS | QSSSNCSNPI | SVPLRRHHLN | NPPPSQVGLT | 301 |
| RRSRTESITA | TSPASMVGGK | PGSFRVRASS | DGEGTMSRPA | SVDGSPVSPS | TNRTHAHRHR | 361 |
| GSARLHPPLN | HSRSIPMPAS | RCSPSATSPV | SLSSSSTSGH | GSTSDCLFPR | RSSASVSGSP | 421 |
| SDGGFISSDE | YGSSPCDFRS | SFRSVTPDSL | GHTPPARGEE | ELSNYICMGG | KGPSTLTAPN | 481 |
| GHYILSRGGN | GHRCTPGTGL | GTSPALAGDE | AASAADLDNR | FRKRTHSAGT | SPTITHQKTP | 541 |

TABLE 5-continued

Human IRS-1 amino acid sequence

| | | | | | |
|---|---|---|---|---|---|
| SQSSVASIEE | YTEMMPAYPP | GGGSGGRLPG | HRHSAFVPTR | SYPEEGLEMH | PLERRGGHHR | 601 |
| PDSSTLHTDD | GYMPMSPGVA | PVPSGRKGSG | DYMPMSPKSV | SAPQQIINPI | RRHPQRVDPN | 661 |
| GYMMMSPSGG | CSPDIGGGPS | SSSSSSNAVP | SGTSYGKLWT | NGVGGHHSHV | LPHPKPPVES | 721 |
| SGGKLLPCTG | DYMNMSPVGD | SNTSSPSDCY | YGPEDPQHKP | VLSYYSLPRS | FKHTQRPGEP | 781 |
| EEGARHQHLR | LSTSSGRLLY | AATADDSSSS | TSSDSLGGGY | CGARLEPSLP | HPHHQVLQPH | 841 |
| LPRKVDTAAQ | TNSRLARPTR | LSLGDPKAST | LPRAREQQQQ | QQPLLHPPEP | KSPGE<u>YVNIE</u> | 901 |
| FGSDQSGYLS | GPVAFHSSPS | VRCPSQLQPA | PREEETGTEE | YMKMDLGPGR | RAAWQESTGV | 961 |
| EMGRLGPAPP | GAASICRPTR | AVPSSRGDYM | TMQMSCPRQS | YVDTSPAAPV | SYADMRTGIA | 1021 |
| AEEVSLPRAT | MAAASSSSAA | SASPTGPQGA | AELAAHSSLL | GGPQGPGGMS | AFTRVNLSPN | 1081 |
| RNQSAKVIRA | DPQGCRRRHS | SETFSSTPSA | TRVGNTVPFG | AGAAVGGGGG | SSSSSEDVKR | 1141 |
| HSSASFENVW | LRPGELGGAP | KEPAKLCGAA | GGLENGLN<u>YI</u> | <u>DL</u>DLVKDFKQ | CPQECTPEPQ | 1201 |
| PPPPPPPHQP | LGSGESSSTR | RSSEDLSAYA | SISFQKQPED | RQ | | |

(SEQ ID NO:5; GENBANK Accession No. JS0670; pleckstrin domain spans residues 11–113, inclusive; Phosphate-binding residues include 46, 465, 551, 612, 632, 662, 732, 941, 989, or 1012 of SEQ ID NO: 5)

TABLE 6

Human IRS-1 cDNA

| | | | | | |
|---|---|---|---|---|---|
| cggcggcgcg | gtcggagggg | gccggcgcgc | agagccagac | gccgccgctt | gttttggttg | 61 |
| gggctctcgg | caactctccg | aggaggagga | ggaggaggga | ggaggggaga | agtaactgca | 121 |
| gcggcagcgc | cctcccgagg | aacaggcgtc | ttccccgaac | ccttcccaaa | cctcccccat | 181 |
| cccctctcgc | ccttgtcccc | tcccctcctc | cccagccgcc | tggagcgagg | gcagggatg | 241 |
| agtctgtccc | tccggccggt | ccccagctgc | agtggctgcc | cggtatcgtt | tcgcatggaa | 301 |
| aagccacttt | ctccacccgc | cgagatgggc | ccggatgggg | ctgcagagga | cgcgcccgcg | 361 |
| ggcggcggca | gcagcagcag | cagcagcagc | agcaacagca | acagccgcag | cgccgcggtc | 421 |
| tctgcgactg | agctggtatt | tgggcggctg | gtggcggctg | ggacggttgg | ggggtgggag | 481 |
| gaggcgaagg | aggagggaga | accccgtgca | acgttgggac | ttggcaaccc | gcctcccct | 541 |
| gcccaaggat | atttaatttg | cctcgggaat | cgctgcttcc | agaggggaac | tcaggaggga | 601 |
| aggcgcgcgc | gcgcgcgcgc | tcctggaggg | gcaccgcagg | gaccccgac | tgtcgcctcc | 661 |
| ctgtgccgga | ctccagccgg | ggcgacgaga | gatgcatctt | cgctccttcc | tggtggcggc | 721 |
| ggcggctgag | aggagacttg | gctctcggag | gatcggggct | gccctcaccc | cggacgcact | 781 |
| gcctccccgc | cggcgtgaag | cgcccgaaaa | ctccggtcgg | gctctctcct | gggctcagca | 841 |
| gctgcgtcct | ccttcagctg | cccctccccg | gcgcgggggg | cggcgtggat | ttcagagtcg | 901 |
| gggtttctgc | tgcctccagc | cctgtttgca | tgtgccgggc | gcggcgagg | agcctccgcc | 961 |
| ccccacccgg | ttgttttcg | gagcctccct | ctgctcagcg | ttggtggtgg | cggtggcagc | 1021 |
| atggcgagcc | ctccggagag | cgatggcttc | tcggacgtgc | gcaaggtggg | ctacctgcgc | 1081 |
| aaacccaaga | gcatgcacaa | acgcttcttc | gtactgcgcg | cggccagcga | ggctggggc | 1141 |
| ccggcgcgcc | tcgagtacta | cgagaacgag | aagaagtggc | ggcacaagtc | gagcgccccc | 1201 |
| aaacgctcga | tcccccttga | gagctgcttc | aacatcaaca | gcgggctga | ctccaagaac | 1261 |
| aagcacctgg | tggctctcta | cacccgggac | gagcactttg | ccatcgcggc | ggacagcgag | 1321 |

TABLE 6-continued

Human IRS-1 cDNA

| | | | | | |
|---|---|---|---|---|---|
| gccgagcaag | acagctggta | ccaggctctc | ctacagctgc | acaaccgtgc | taagggccac | 1381 |
| cacgacggag | ctgcggccct | cggggcggga | ggtggtgggg | gcagctgcag | cggcagctcc | 1441 |
| ggccttggtg | aggctgggga | ggacttgagc | tacggtgacg | tgccccccagg | acccgcattc | 1501 |
| aaagaggtct | ggcaagtgat | cctgaagccc | aagggcctgg | gtcagacaaa | gaacctgatt | 1561 |
| ggtatctacc | gcctttgcct | gaccagcaag | accatcagct | tcgtgaagct | gaactcggag | 1621 |
| gcagcggccg | tggtgctgca | gctgatgaac | atcaggcgct | gtggccactc | ggaaaacttc | 1681 |
| ttcttcatcg | aggtggggcg | ttctgccgtg | acggggcccg | gggagttctg | gatgcaggtg | 1741 |
| gatgactctg | tggtggccca | gaacatgcac | gagaccatcc | tggaggccat | gcgggccatg | 1801 |
| agtgatgagt | tccgccctcg | cagcaagagc | cagtcctcgt | ccaactgctc | taaccccatc | 1861 |
| agcgtccccc | tgcgccggca | ccatctcaac | aatccccgc | ccagccaggt | ggggctgacc | 1921 |
| cgccgatcac | gcactgagag | catcaccgcc | acctccccgg | ccagcatggt | gggcgggaag | 1981 |
| ccaggctcct | tccgtgtccg | cgcctccagt | gacggcgaag | gcaccatgtc | ccgcccagcc | 2041 |
| tcggtggacg | gcagccctgt | gagtcccagc | accaacagaa | cccacgccca | ccggcatcgg | 2101 |
| ggcagcgccc | ggctgcaccc | cccgctcaac | cacagccgct | ccatccccat | gccggcttcc | 2161 |
| cgctgctcgc | cttcggccac | cagcccggtc | agtctgtcgt | ccagtagcac | cagtggccat | 2221 |
| ggctccacct | cggattgtct | cttcccacgg | cgatctagtg | cttcggtgtc | tggttccccc | 2281 |
| agcgatggcg | gtttcatctc | ctcggatgag | tatggctcca | gtccctgcga | tttccggagt | 2341 |
| tccttccgca | gtgtcactcc | ggattccctg | ggccacaccc | caccagcccg | cggtgaggag | 2401 |
| gagctaagca | actatatctg | catgggtggc | aaggggccct | ccaccctgac | cgcccccaac | 2461 |
| ggtcactaca | ttttgtctcg | gggtggcaat | ggccaccgct | gcaccccagg | aacaggcttg | 2521 |
| ggcacgagtc | cagccttggc | tggggatgaa | gcagccagtg | ctgcagatct | ggataatcgg | 2581 |
| ttccgaaaga | gaactcactc | ggcaggcaca | tccctacca | ttacccacca | gaagaccccg | 2641 |
| tcccagtcct | cagtggcttc | cattgaggag | tacacagaga | tgatgcctgc | ctacccacca | 2701 |
| ggaggtggca | gtggaggccg | actgccggga | cacaggcact | ccgccttcgt | gcccacccgc | 2761 |
| tcctacccag | aggagggtct | ggaaatgcac | cccttggagc | gtcggggggg | gcaccaccgc | 2821 |
| ccagacagct | ccaccctcca | cacggatgat | ggctacatgc | ccatgtcccc | agggtggcc | 2881 |
| ccagtgccca | gtggccgaaa | gggcagtgga | gactatatgc | ccatgagccc | caagagcgta | 2941 |
| tctgccccac | agcagatcat | caatcccatc | agacgccatc | cccagagagt | ggaccccaat | 3001 |
| ggctacatga | tgatgtcccc | cagcggtggc | tgctctcctg | acattggagg | tggccccagc | 3061 |
| agcagcagca | gcagcagcaa | cgccgtccct | tccgggacca | gctatggaaa | gctgtggaca | 3121 |
| aacgggtag | ggggccacca | ctctcatgtc | ttgcctcacc | ccaaaccccc | agtgagagc | 3181 |
| agcggtggta | agctcttacc | ttgcacaggt | gactacatga | acatgtcacc | agtggggac | 3241 |
| tccaacacca | gcagccctc | cgactgctac | tacggccctg | aggacccca | gcacaagcca | 3301 |
| gtcctctcct | actactcatt | gccaagatcc | tttaagcaca | cccagcgccc | cggggagccg | 3361 |
| gaggagggtg | cccggcatca | gcacctccgc | ctttccacta | gctctggtcg | ccttctctat | 3421 |
| gctgcaacag | cagatgattc | ttcctcttcc | accagcagcac | acagcctggg | tgggggatac | 3481 |
| tgcgggcta | ggctggagcc | cagccttcca | catccccacc | atcaggttct | gcagccccat | 3541 |
| ctgcctcgaa | aggtggacac | agctgctcag | accaatagcc | gcctggccg | gcccacgagg | 3601 |

TABLE 6-continued

Human IRS-1 cDNA

| | | | | |
|---|---|---|---|---|
| ctgtccctgg | gggatcccaa | ggccagcacc | ttacctcggg | cccgagagca gcagcagcag | 3661 |
| cagcagccct | tgctgcaccc | tccagagccc | aagagcccgg | gggaatatgt caatattgaa | 3721 |
| tttgggagtg | atcagtctgg | ctacttgtct | ggcccggtgg | cttccacag ctcaccttct | 3781 |
| gtcaggtgtc | catcccagct | ccagccagct | cccagagagg | aagagactgg cactgaggag | 3841 |
| tacatgaaga | tggacctggg | gccgggccgg | agggcagcct | gcaggagag cactggggtc | 3901 |
| gagatgggca | gactgggccc | tgcacctccc | ggggctgcta | gcatttgcag gcctacccgg | 3961 |
| gcagtgccca | gcagccgggg | tgactacatg | accatgcaga | tgagttgtcc ccgtcagagc | 4021 |
| tacgtggaca | cctcgccagc | tgcccctgta | agctatgctg | acatgcgaac aggcattgct | 4081 |
| gcagaggagg | tgagcctgcc | cagggccacc | atggctgctg | cctcctcatc ctcagcagcc | 4141 |
| tctgcttccc | cgactgggcc | tcaaggggca | gcagagctgg | ctgcccactc gtccctgctg | 4201 |
| gggggcccac | aaggacctgg | gggcatgagc | gccttcaccc | gggtgaacct cagtcctaac | 4261 |
| cgcaaccaga | gtgccaaagt | gatccgtgca | gacccacaag | ggtgccggcg gaggcatagc | 4321 |
| tccgagactt | tctcctcaac | acccagtgcc | acccggggtgg | gcaacacagt gccctttgga | 4381 |
| gcggggggcag | cagtagggggg | cggtggcggt | agcagcagca | gcagcgagga tgtgaaacgc | 4441 |
| cacagctctg | cttcccttga | gaatgtgtgg | ctgaggcctg | gggagcttgg gggagccccc | 4501 |
| aaggagccag | ccaaactgtg | tgggctgct | ggggtttgg | agaatggtct taactacata | 4561 |
| gacctggatt | tggtcaagga | cttcaaacag | tgccctcagg | agtgcacccc tgaaccgcag | 4621 |
| cctccccac | ccccacccc | tcatcaaccc | ctgggcagcg | gtgagagcag ctccacccgc | 4681 |
| cgctcaagtg | aggatttaag | cgcctatgcc | agcatcagtt | ccagaagca gccagaggac | 4741 |
| cgtcagtagc | tcaactggac | atcacagcag | aatgaagacc | taaatgacct cagcaaatcc | 4801 |
| tcttctaact | catgggtacc | cagactctaa | atatttcatg | attcacaact aggacctcat | 4861 |
| atcttcctca | tcagtagatg | gtacgatgca | tccatttcag | tttgtttact ttatccaatc | 4921 |
| ctcaggattt | cattgactga | actgcacgtt | ctatattgtg | ccaagcgaaa aaaaaaaatg | 4981 |
| cactgtgaca | ccagaataat | gagtctgcat | aaacttcatc | ttcaaccta aggcttagc | 5041 |
| tggccacagt | gagctgatgt | gcccaccacc | gtgtcatgag | agaatgggtt tactctcaat | 5101 |
| gcattttcaa | gatacatttc | atctgctgct | gaaactgtgt | acgacaaagc atcattgtaa | 5161 |
| attatttcat | acaaaactgt | tcacgttggg | tggagagagt | attaaatatt taacataggt | 5221 |
| tttgatttat | atgtgtaatt | ttttaaatga | aaatgtaact | tttcttacag cacatctttt | 5281 |
| ttttggatgt | gggatggagg | tatacaatgt | tctgttgtaa | agagtggagc aaatgcttaa | 5341 |
| aacaaggctt | aaaagagtag | aataggtat | gatccttgtt | ttaagattgt aattcagaaa | 5401 |
| acataatata | agaatcatag | tgccatagat | ggttctcaat | tgtatagtta tatttgctga | 5461 |
| tactatctct | tgtcatataa | acctgatgtt | gagctgagtt | ccttataaga attaatctta | 5521 |
| attttgtatt | ttttcctgta | agacaatagg | ccatgttaat | taaactgaag aaggatatat | 5581 |
| ttggctgggt | gttttcaaat | gtcagcttaa | aattggtaat | tgaatggaag caaaattata | 5641 |
| agaagaggaa | attaaagtct | tccattgcat | gtattgtaaa | cagaaggaga tgggtgattc | 5701 |
| cttcaattca | aaagctctct | ttggaatgaa | caatgtgggc | gtttgtaaat tctggaaatg | 5761 |
| tctttctatt | cataataaac | tagatactgt | tgatctttta | aaaaaaaaa aaaaaaaaa | 5821 |
| aaaaaaaa | | | | |

(SEQ ID NO:6; GENBANK Accession No. NM 005544)

The double mutation of tyrosine 897 and 1180 was constructed by replacement of 3'-sequences coding 897F by the same region of 1180F using restriction enzymes NheI and EcoRI, and this construct was called 897F1180F or ΔGrb2 ΔSyp. The expression plasmids were under control of a CMV promoter (hIRS-1-wt, ΔGrb2, ΔSyp, ΔGrb2, ΔSyp and pBK-CMV (mock) and linearized at the 3'-end of poly A signal sequences by MluI restriction enzymes followed by purification. A similar approach was used to change the tyrosine residue to phenyalanine at positions 613 and 942 to create the double PI3K mutant construct (ΔPI3K). The hIRS-1 mutants have a FLAG epitope (DYKDDDDK (SEQ ID NO:6) +stop codon) added to the C-terminus by PCR.

This strategy allows to distinguish the mutant protein from "wild type" hIRS-1 in stable transfected cell lines. The mutants are used to define the link between the IRS signal transduction pathway and activation of HAAH as a downstream effector gene and identify compounds to inhibit transduction along the pathway to inhibit growth of tumors characterized by HAAH overexpression. Antibodies or other compounds which bind to phosphorylation sites or inhibit phosphorylation at those sites are used to inhibit signal transduction and thus proleferation of HAA-overexpressing tumors.

Other embodiments are within the following claims.

What is claimed is:

1. A method of inhibiting tumor growth in a mammal comprising administering to said mammal a dominant negative mutant of HAAH, wherein said HAAH comprises the amino acid sequence of SEQ ID NO:2, and wherein said mutant comprises a mutation, said mutation consisting of a substitution or deletion of a single amino acid at residue 679 of SEQ ID NO:2.

2. A method of inhibiting tumor growth in a mammal comprising administering to said mammal a dominant negative mutant of HAAH, wherein said HAAH comprises the amino acid sequence of SEQ ID NO:2, and wherein said mutant comprises a mutation, said mutation consisting of a substitution or deletion of a single amino acid at residue 690 of SEQ ID NO:2.

3. The method of claim 1 or 2, wherein said mutant is administered directly into the tumor site.

4. The method of claim 1 or 2, wherein said mutant is administered systemically.

5. The method of claim 1 or 2, wherein said tumor is selected from the group consisting of colon cancer, breast cancer, pancreatic cancer, liver cancer, and cancer of the bile ducts.

6. The method of claim 1 or 2, wherein said tumor is a cancer of the central nervous system.

7. The method of claim 1 or 2, wherein said tumor is a hepatocellular carcinoma.

8. The method of claim 1 or 2, wherein said tumor is a cholangiocarcinoma.

9. The method of claim 1 or 2, wherein said tumor is a glioblastoma.

10. The method of claim 1 or 2, wherein said tumor is a neuroblastoma.

11. A method of inhibiting growth of a tumor in a mammal comprising administering to said mammal an antibody selected from the group consisting of 5C7 produced by hybridoma ATCC designation PTA 3383, 19B produced by hybridoma ATCC designation 3384, and 86A produced by hybridoma ATCC designation 3385.

12. The method of claim 11, wherein said antibody is 5C7.

13. The method of claim 11, wherein said antibody is 19B.

14. The method of claim 11, wherein said antibody is 86A.

* * * * *